US010449243B2

(12) United States Patent
Casimiro et al.

(10) Patent No.: US 10,449,243 B2
(45) **Date of Patent: *Oct. 22, 2019**

(54) DENGUE VIRUS VACCINE COMPOSITIONS AND METHODS OF USE THEREOF

(71) Applicants: Merck Sharp & Dohme Corp., Rahway, NJ (US); Danilo R. Casimiro, Harleysville, PA (US); Andrew Bett, Lansdale, PA (US); Beth-Ann Griswold Coller, Belle Mead, NJ (US); Govindarajan Dhanasekaran, Harleysville, PA (US); Ramesh V. Chintala, Chalfont, PA (US)

(72) Inventors: Danilo R. Casimiro, Harleysville, PA (US); Andrew Bett, Lansdale, PA (US); Beth-Ann Griswold Coller, Belle Mead, NJ (US); Govindarajan Dhanasekaran, Harleysville, PA (US); Ramesh V. Chintala, Chalfont, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/536,319

(22) PCT Filed: Dec. 18, 2015

(86) PCT No.: PCT/US2015/066549

§ 371 (c)(1),
(2) Date: Jun. 15, 2017

(87) PCT Pub. No.: WO2016/106107

PCT Pub. Date: Jun. 30, 2016

(65) Prior Publication Data

US 2017/0360917 A1 Dec. 21, 2017

Related U.S. Application Data

(60) Provisional application No. 62/095,331, filed on Dec. 22, 2014.

(51) Int. Cl.

| | |
|---|---|
| *A61K 39/12* | (2006.01) |
| *C12N 7/00* | (2006.01) |
| *A61K 39/00* | (2006.01) |

(52) U.S. Cl.

CPC ................ *A61K 39/12* (2013.01); *C12N 7/00* (2013.01); *A61K 2039/5252* (2013.01);

(Continued)

(58) Field of Classification Search

CPC ................ A61K 39/12; A61K 2039/70; A61K 2039/5252; A61K 2039/55505; A61K 2039/575; A61K 2039/545; A61K 2039/5254; A61K 2039/55577; A61K 39/39; A61K 2039/55511; A61K 2039/6075; A61K 2039/525; A61K 2039/52524; C12N 7/00; C12N 2770/24171; C12N 2770/24122; C12N 2770/24134; C12N 15/1131; C12N 15/86;

(Continued)

(56) References Cited

U.S. PATENT DOCUMENTS

| | | | |
|---|---|---|---|
| 6,184,024 | B1 | 2/2001 | Lai |
| 9,198,964 | B2 | 12/2015 | Coller et al. |

(Continued)

FOREIGN PATENT DOCUMENTS

| | | |
|---|---|---|
| EP | 2484376 | 8/2012 |
| WO | WO9640933 | 12/1996 |

(Continued)

OTHER PUBLICATIONS

Durbin AP, Kirkpatrick BD, Pierce KK, Elwood D, Larsson CJ, Lindow JC, et. al. A single dose of any of four different live attenuated tetravalent dengue vaccines is safe and immunogenic in flavivirus-naive adults: a randomized, double-blind clinical trial. J Infect Dis. Mar. 15, 2013;207(6):957-65. Epub Jan. 17, 2013.*
Bray, Michael et al., Construction of intertypic chimeric dengue viruses by substitution of structural protein genes, Proc. Natl. Acad. Sci. USA, 1991, 10342-10346, 88.
Bray, Michael et al., Monkeys Immunized with Intertypic Chimeric Dengue Viruses are Protected against Wild-Type Virus Challenge, Journal of Virology, 1996, 4162-4166, 70(6).
Chen, Weiran et al., Construction of Intertypic Chimeric Dengue Viruses Exhibiting Type 3 Antigenicity and Neurovirulence for Mice, Journal of Virology, 1996, 5186-5190, 69(8).

(Continued)

*Primary Examiner* — Rachel B Gill
(74) *Attorney, Agent, or Firm* — Matthew A. Leff; Laura M. Ginkel

(57) ABSTRACT

The present invention relates to dengue virus vaccine compositions comprising a first and a second dengue vaccine, wherein the first dengue vaccine comprises at least one live, attenuated dengue virus or live, attenuated chimeric dengue virus and the second dengue vaccine is a recombinant dengue subunit vaccine, a DNA vaccine, a conjugate vaccine, or an inactivated dengue vaccine; wherein the genome of the live attenuated dengue virus or the live attenuated chimeric dengue virus comprises a 30 nucleotide deletion of the TL2 stem-loop structure of the 3' untranslated region. The dengue virus vaccine compositions of the invention may further comprise one or more adjuvants. In preferred embodiments of the invention, the first and the second dengue vaccine are tetravalent. The invention also relates to methods of using the dengue virus vaccine compositions of the invention to treat or prevent dengue infection, or to prevent, ameliorate, or delay the onset or progression of the clinical manifestations thereof.

19 Claims, 8 Drawing Sheets

Specification includes a Sequence Listing.

(52) U.S. Cl.
CPC ................. *A61K 2039/5254* (2013.01); *A61K 2039/545* (2013.01); *A61K 2039/55505* (2013.01); *A61K 2039/55577* (2013.01); *A61K 2039/575* (2013.01); *A61K 2039/70* (2013.01); *C12N 2770/24122* (2013.01); *C12N 2770/24134* (2013.01); *C12N 2770/24171* (2013.01); *Y02A 50/386* (2018.01)

(58) Field of Classification Search
CPC ........ C12N 2770/24151; Y02A 50/386; C07K 14/005
See application file for complete search history.

(56) References Cited

U.S. PATENT DOCUMENTS

| | | | |
|---|---|---|---|
| 2007/0087015 A1 | 4/2007 | Eckels, II et al. |
| 2009/0258036 A1 | 10/2009 | Whitehead et al. |
| 2010/0104598 A1 | 4/2010 | Whitehead et al. |
| 2010/0230612 A1 | 9/2010 | Guy et al. |
| 2012/0251570 A1 | 10/2012 | Alver et al. |
| 2012/0294889 A1 | 11/2012 | Monath et al. |
| 2013/0095136 A1 | 4/2013 | Guirakhoo |
| 2013/0216575 A1 | 8/2013 | Coller et al. |
| 2016/0151477 A1 | 6/2016 | Bett et al. |

FOREIGN PATENT DOCUMENTS

| | | |
|---|---|---|
| WO | WO9837911 | 9/1998 |
| WO | WO0014245 | 3/2000 |
| WO | WO0057907 | 10/2000 |
| WO | WO0057908 | 10/2000 |
| WO | WO0057909 | 10/2000 |
| WO | WO0057910 | 10/2000 |
| WO | WO02095075 | 11/2002 |
| WO | WO03092592 | 11/2003 |
| WO | WO03103571 | 12/2003 |
| WO | WO2006044857 | 4/2006 |
| WO | WO2006134443 | 12/2006 |
| WO | WO2007002470 | 1/2007 |
| WO | WO2007015783 | 2/2007 |
| WO | WO2007141259 | 12/2007 |
| WO | WO2008022196 | 2/2008 |
| WO | WO2008047023 | 4/2008 |
| WO | WO2008127307 | 10/2008 |
| WO | WO2012154202 A1 | 11/2012 |
| WO | WO2014016362 | 1/2014 |
| WO | WO2014204892 | 12/2014 |

OTHER PUBLICATIONS

Ching-Juh Lai et al., Chimeric Flaviviruses: novel vaccines against dengue fever, tick-borne encephalitis, and japanese encephalitis, Advances in Virus Research, 2003, 469-509, 61.

Cuzzubbo, Andrea et al., Use of Recombinant Envelope Proteins for Serological Diagnosis of Dengue Virus Infection in an Immunochromatographic Assay, Clinical and Diagnostic Laboratory Immunology, 2001, 1150-1155, 8(6).

Durbin, Anna P. et al., A Single Dose of Any of Four Different Live Attenuated Tetravalent Dengue Vaccines is Safe and Immunogenic in flavivirus-naive Adults: A Randomized, Double-blind Clinical Trial, J. Infect. Dis., 2013, 957-965, 207.

Durbin, Anna P. et al., Development and clinical evaluation of multiple investigational monovalent DENV vaccines to identify components for inclusion in a live attenuated retravelent DENV vaccine, Vaccine, 2011, 7242-7450, 29.

Guirakhoo, F. et al., Recombinant Chimeric Yellow Fever-Dengue Type 2 Virus is Immunogenic and Protective in Nonhuman Primates, Journal of Virology, 2000, 5477-5485, 74(12).

Guthrie, Alan et al., Protective immunication of horses with a recombinant canarypox virus vectored vaccine co-expressing genes encoding the outer capsid proteins of African horse sickness virus, Vaccine;, 2009, 4434-4438, 27.

Guy, Bruno et al., Preclinical and clinical development of YFV 17D-based chimeric vaccines against dengue, West Nile and Japaese encephalitis viruses, Vaccine;, 2010, 632-649, 28.

Heinz, Franz et al., Flaviviruses and flavivirus vaccines, Vaccine;, 2012, 4301-4306, 30.

Lai, C.J., et al., Evaluation of molecular strategies to develop a live dengue vaccine, Clinical and Diagnostic Virology, 1998, 173-179, 10.

Simmons, M. et al., Protection against dengue virus by non-replicating and live attenuated vaccines used together in a prime boost vaccination strategy, Virology, 2009, 280-288, 396(2).

Casimiro, D.R. et al., Abstract—Pre-Clinical Evaluation of a Combined Liver Attentuated (LAV) and Subunit (DEN-80E) Prime-Boost Vaccine Approach Against Dengue, Poster Presentation at 2014 American Society of Tropical Medicine and Hygience, New Orleans, Nov. 2-4, 2014, 1-2.

Azevedo, Adriana S. et al., The Synergi sti c Effect of Combi ned Immuni zati on wi th a DNA Vacci ne and Chimeri c Yel l ow Fever/Dengue Vi rus Leads to Strong Protecti on agai nst Dengue, PLOS ON E, 2013, e58357, 8(3).

Blaney, Joseph E. Jr. et al., Dengue virus type 3 vaccine candidates generated by introduction of deletions in the 3 untranslated region (3-UTR) or by exchange of the DENV-3 3-UTR with that of DENV-4, Vaccine, 2008, 817-828, 26.

Blaney, Joseph E. Jr. et al., Genetically Modified, Live Attenuated Dengue Virus Type 3 Vaccine Candidates, The American Society of Tropical Medicine and Hygiene, 2004, 811-821, 71-6.

Blaney, Joseph E. Jr. et al., Vaccine candidates derived from a novel infectious cDNA clone of an American genotype dengue virus type 2, BMC Infectious Disease, 2004, 1-10, 4-39.

Coller, Beth-Ann G. et al., The development of recombinant subunit envelope-based vaccines to protect against dengue virus induced disease, Vaccine, 2011, 7267-7275, 29(42).

Durbin, Anna P. et al., rDEN4D30, a Live Attenuated Dengue Virus Type 4 Vaccine Candidate, is Safe, Immunogenic, and Highly Infectious in Healthy Adult Volunteers, the Journal of Infectious Diseases, 2005, 710-718, 191.

Kirkpatrick, Beth D.et al., Robust and Balanced Immune Responses to All 4 Dengue Virus Serotypes Following Administration of a Single Dose of a Live Attenuated Tetravalent Dengue Vaccine to Healthy, Flavivirus-Naive Adults, The Journal of Infectious Diseases, 2015, 702-710, 212.

Minke JM, et al., Protection provided by a recombinant ALVAC-WNV vaccine expressing the prM/E genes of a lineage 1 strain of WNV against a virulent challenge with a lineage 2 strain, Vaccine, 2011, 4608-4612, 29.

Minke JM, et al., Use of DNA and recombinant canarypox viral (ALVAC) vectors for equine herpes virus vaccination, Veterinary Immunology and immunopathology, 2006, 47-57, 111.

Whitehead, S. S. et al., A live, attenuated dengue virus type I vaccine candidate with a 30-nucleotide deletion in the 3' untranslated region is highly attenuated and immunogenic in monkeys, journal of Virology, The American Society or Microbiology, 2003, 1653-1657, 77(2).

Whitehead, SS, Development of TV003/TV005, a single dose, highly immunogenic live attenuated dengue vaccine; what makes this vaccine different from the Sanofi-Pasteur CYD™ in vaccine?, Expert Review of Vaccines, 2016, 509-517, 15-4.

* cited by examiner

MAA: Merck Aluminum Adjuvant
3X MAA: 3 times the dose of MAA
IMX: ISCOMATRIX™ Adjuvant
PBS: Phosphate buffered saline

| Group | Monkeys Per Group | Formulation/Schedule | | Anti-DENV-1 $LiCor_{50}$ Titers (GMT) | Anti-DENV-2 $LiCor_{50}$ Titers (GMT) | Anti-DENV-3 $LiCor_{50}$ Titers (GMT) | Anti-DENV-4 $LiCor_{50}$ Titers (GMT) |
|---|---|---|---|---|---|---|---|
| | | Week 0 | Week 16 | | | | |
| 1 | 4 | Δ30 LATV (10e5 pfu each) Administered SC (0.5 ml) | Δ30 LATV (10e5 pfu each) Administered SC (0.5 ml) | 113 | 190 | 57 | 34 |
| 2 | 4 | Δ30 LATV (10e5 pfu each) Administered SC (0.5 ml) | Tetravalent DEN-80E (10, 10, 10, 20 μg each 80E) /Alhydrogel® (225 μg) Administered IM (0.5ml) | 135 | 226 | 135 | 17 |
| 3 | 4 | Δ30 LATV (10e5 pfu each) /Tetravalent DEN-80E (10, 10, 10, 20 μg each 80E) /Alhydrogel® (225 μ g) Administered IM (0.5ml) | Δ30 LATV (10e5 pfu each) /Tetravalent DEN-80E (10, 10, 10, 20 μg each 80E) /Alhydrogel® (225 μg) Administered IM (0.5ml) | 57 | 320 | 80 | 95 |

$LiCor_{50}$ result of <10 considered 5 for purposes of calculating GMT.

FIG. 3

| Group | Monkeys Per Group | Formulation/Schedule | | Anti-DENV-1 $LiCor_{50}$ Titers (GMT) | Anti-DENV-2 $LiCor_{50}$ Titers (GMT) | Anti-DENV-3 $LiCor_{50}$ Titers (GMT) | Anti-DENV-4 $LiCor_{50}$ Titers (GMT) |
|---|---|---|---|---|---|---|---|
| | | Week 0 | Week 24 | | | | |
| 1 | 4 | Δ30 LATV (10e5 pfu each) Admisistered SC (0.5 ml) | Δ30 LATV (10e5 pfu each) Admisistered SC (0.5 ml) | 135 | 113 | 160 | 135 |
| 2 | 4 | Δ30 LATV (10e5 pfu each) Admisistered SC (0.5 ml) | Tetravalent DEN-80E (10, 10, 10, 20 μg each 80E) /Alhydrogel (225 μg) Admisistered IM (0.5 ml) | 320 | 381 | 453 | 226 |
| 3 | 4 | Δ30 LATV (10e5 pfu each) /Tetravalent DEN-80E (10, 10, 10, 20 μg each 80E) /Alhydrogel (225 μg) Admisistered IM (0.5 ml) | Δ30 LATV (10e5 pfu each) /Tetravalent DEN-80E (10, 10, 10, 20 μg each 80E) /Alhydrogel (225 μg) Admisistered IM (0.5 ml) | 640 | 761 | 1076 | 640 |

$LiCor_{50}$ result of <10 considered 5 for purposes of calculating GMT

FIG.4

Dengue Serotype Neutralizing Antibody Titers ($LiCor_{50}$ GMT) Induced in Rhesus Macaques at Week 4 (4 weeks post dose 1)

| Group | Monkeys Per Group | Formulation/Schedule | | Anti–DENV–1 $LiCor_{50}$ Titers (GMT) | Anti–DENV–2 $LiCor_{50}$ Titers (GMT) | Anti–DENV–3 $LiCor_{50}$ Titers (GMT) | Anti–DENV–4 $LiCor_{50}$ Titers (GMT) |
|---|---|---|---|---|---|---|---|
| | | Week 0 | Week 24 | | | | |
| 1 | 5 | Tetravalent LAV (10e5 pfu each) Administered SC (0.5 ml) | Tetravalent LAV (10e5 pfu each) Administered SC (0.5 ml) | 92 | 160 | 80 | 279 |
| 2 | 5 | Tetravalent LAV (10e5 pfu each) / Tetravalent DEN–80E (10, 10, 10, 20 μg each 80E) / Alhydrogel (225 μg) Administered IM (0.5 ml) | Tetravalent LAV (10e5 pfu each) / Tetravalent DEN–80E (10, 10, 10, 20 μg each 80E) / Alhydrogel (225 μg) Administered IM (0.5 ml) | 121 | 243 | 106 | 320 |
| 3 | 5 | Tetravalent LAV (10e5 pfu each) / Tetravalent DEN–80E (3, 3, 3, 6 μg each 80E) / Alhydrogel (225 μg) Administered IM (0.5 ml) | Tetravalent LAV (10e5 pfu each) / Tetravalent DEN–80E (3, 3, 3, 6 μg each 80E) / Alhydrogel (225 μg) Administered IM (0.5 ml) | 279 | 557 | 211 | 422 |
| 4 | 5 | Tetravalent LAV (10e3 pfu each) / Tetravalent DEN–80E (10, 10, 10, 20 μg each 80E) / Alhydrogel (225 μg) Administered IM (0.5 ml) | Tetravalent LAV (10e3 pfu each) / Tetravalent DEN–80E (10, 10, 10, 20 μg each 80E) / Alhydrogel (225 μg) Administered IM (0.5 ml) | 53 | 229 | 121 | 243 |
| $LiCor_{50}$ result of <10 considered 5 for purposes of calculating GMT. | | | | | | | |

FIG.6

Dengue Serotype Neutralizing Antibody Titers ($LiCor_{50}$ GMT) Induced in Rhesus Macaques at Week 28 (4 weeks post dose 2)

| Group | Monkeys Per Group | Formulation/Schedule | | Anti-DENV-1 $LiCor_{50}$ Titers (GMT) | Anti-DENV-2 $LiCor_{50}$ Titers (GMT) | Anti-DENV-3 $LiCor_{50}$ Titers (GMT) | Anti-DENV-4 $LiCor_{50}$ Titers (GMT) |
|---|---|---|---|---|---|---|---|
| | | Week 0 | Week 24 | | | | |
| 1 | 5 | Tetravalent LAV (10e5 pfu each) Administered SC (0.5 ml) | Tetravalent LAV (10e5 pfu each) Administered SC (0.5 ml) | 68 | 1280 | 485 | 640 |
| 2 | 5 | Tetravalent LAV (10e5 pfu each) / Tetravalent DEN-80E (10, 10, 10, 20 μg each 80E) / Alhydrogel (225 μg) Administered IM (0.5 ml) | Tetravalent LAV (10e5 pfu each) / Tetravalent DEN-80E (10, 10, 10, 20 μg each 80E) / Alhydrogel (225 μg) Administered IM (0.5 ml) | 3378 | 5881 | 3378 | 7760 |
| 3 | 5 | Tetravalent LAV (10e5 pfu each) / Tetravalent DEN-80E (3, 3, 3, 6 μg each 80E) / Alhydrogel (225 μg) Administered IM (0.5 ml) | Tetravalent LAV (10e5 pfu each) / Tetravalent DEN-80E (3, 3, 3, 6 μg each 80E) / Alhydrogel (225 μg) Administered IM (0.5 ml) | 1689 | 3378 | 8914 | 5881 |
| 4 | 5 | Tetravalent LAV (10e3 pfu each) / Tetravalent DEN-80E (10, 10, 10, 20 μg each 80E) / Alhydrogel (225 μg) Administered IM (0.5 ml) | Tetravalent LAV (10e3 pfu each) / Tetravalent DEN-80E (10, 10, 10, 20 μg each 80E) / Alhydrogel (225 μg) Administered IM (0.5 ml) | 1470 | 3378 | 1689 | 1689 |

$LiCor_{50}$ result of <10 considered 5 for purposes of calculating GMT.

FIG. 7

SEQUENCE LISTING

```
<160> NUMBER OF SEQ ID NOS: 5

<210> SEQ ID NO 1
<211> LENGTH: 395
<212> TYPE: PRT
<213> ORGANISM: Dengue 1

<400> SEQUENCE: 1

Met Arg Cys Val Gly Ile Gly Ser Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45
```

-continued

```
Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Ala Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
    130                 135                 140

Thr Gly Asp Gln His Gln Val Gly Asn Glu Ser Thr Glu His Gly Thr
145                 150                 155                 160

Thr Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Thr Met Lys Glu Lys Ser Trp Leu Val
        195                 200                 205

His Lys Gln Trp Phe Leu Asp Leu Pro Leu Pro Trp Thr Ser Gly Ala
    210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Thr Leu Lys Gly Met Ser Tyr Val Met Cys Thr Gly
    290                 295                 300

Ser Phe Lys Leu Glu Lys Glu Val Ala Glu Thr Gln His Gly Thr Val
305                 310                 315                 320

Leu Val Gln Ile Lys Tyr Glu Gly Thr Asp Ala Pro Cys Lys Ile Pro
                325                 330                 335

Phe Ser Thr Gln Asp Glu Arg Gly Val Thr Gln Asn Gly Arg Leu Ile
            340                 345                 350

Thr Ala Asn Pro Ile Val Thr Asp Lys Glu Lys Pro Val Asn Ile Glu
        355                 360                 365

Ala Glu Pro Pro Phe Gly Glu Ser Tyr Ile Val Ile Gly Ala Gly Glu
    370                 375                 380

Lys Ala Leu Lys Leu Ser Trp Phe Lys Lys Gly
385                 390                 395


<210> SEQ ID NO 2
<211> LENGTH: 395
<212> TYPE: PRT
<213> ORGANISM: Dengue 2

<400> SEQUENCE: 2

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30
```

```
Thr Met Ala Lys Asn Lys Pro Thr Leu Asp Phe Glu Leu Ile Lys Thr
        35                  40                  45

Glu Ala Lys Gln Pro Ala Thr Leu Arg Lys Tyr Cys Ile Glu Ala Lys
    50                  55                  60

Leu Thr Asn Thr Thr Thr Asp Ser Arg Cys Pro Thr Gln Gly Glu Pro
65                  70                  75                  80

Thr Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Met Phe Thr Cys Lys Lys Asn Met Glu Gly Lys
        115                 120                 125

Ile Val Gln Pro Glu Asn Leu Glu Tyr Thr Val Val Ile Thr Pro His
    130                 135                 140

Ser Gly Glu Glu His Ala Val Gly Asn Asp Thr Gly Lys His Gly Lys
145                 150                 155                 160

Glu Val Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Lys Asp Lys Ala Trp Leu Val
        195                 200                 205

His Arg Gln Trp Phe Leu Asp Leu Pro Leu Pro Trp Leu Pro Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
    290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Ile Gly Val Glu Pro
    370                 375                 380

Gly Gln Leu Lys Leu Asp Trp Phe Lys Lys Gly
385                 390                 395
```

<210> SEQ ID NO 3
<211> LENGTH: 393
<212> TYPE: PRT
<213> ORGANISM: Dengue 3

<400> SEQUENCE: 3

```
Met Arg Cys Val Gly Val Gly Asn Arg Asp Phe Val Glu Gly Leu Ser
```

-continued

```
1               5                   10                  15

Gly Ala Thr Trp Val Asp Val Val Leu Glu His Gly Gly Cys Val Thr
            20                  25                  30

Thr Met Ala Lys Asn Lys Pro Thr Leu Asp Ile Glu Leu Gln Lys Thr
        35                  40                  45

Glu Ala Thr Gln Leu Ala Thr Leu Arg Lys Leu Cys Ile Glu Gly Lys
    50                  55                  60

Ile Thr Asn Ile Thr Thr Asp Ser Arg Cys Pro Thr Gln Gly Glu Ala
65                  70                  75                  80

Ile Leu Pro Glu Glu Gln Asp Gln Asn Tyr Val Cys Lys His Thr Tyr
                85                  90                  95

Val Asp Arg Gly Trp Gly Asn Gly Cys Gly Leu Phe Gly Lys Gly Ser
            100                 105                 110

Leu Val Thr Cys Ala Lys Phe Gln Cys Leu Glu Ser Ile Glu Gly Lys
        115                 120                 125

Val Val Gln His Glu Asn Leu Lys Tyr Thr Val Ile Ile Thr Val His
    130                 135                 140

Thr Gly Asp Gln His Gln Val Gly Asn Glu Thr Gln Gly Val Thr Ala
145                 150                 155                 160

Glu Ile Thr Pro Gln Ala Ser Thr Val Glu Ala Ile Leu Pro Glu Tyr
                165                 170                 175

Gly Thr Leu Gly Leu Glu Cys Ser Pro Arg Thr Gly Leu Asp Phe Asn
            180                 185                 190

Glu Met Ile Leu Leu Thr Met Lys Asn Lys Ala Trp Met Val His Arg
        195                 200                 205

Gln Trp Phe Phe Asp Leu Pro Leu Pro Trp Thr Ser Gly Ala Thr Thr
    210                 215                 220

Glu Thr Pro Thr Trp Asn Arg Lys Glu Leu Leu Val Thr Phe Lys Asn
225                 230                 235                 240

Ala His Ala Lys Lys Gln Glu Val Val Val Leu Gly Ser Gln Glu Gly
                245                 250                 255

Ala Met His Thr Ala Leu Thr Gly Ala Thr Glu Ile Gln Asn Ser Gly
            260                 265                 270

Gly Thr Ser Ile Phe Ala Gly His Leu Lys Cys Arg Leu Lys Met Asp
        275                 280                 285

Lys Leu Glu Leu Lys Gly Met Ser Tyr Ala Met Cys Leu Asn Thr Phe
    290                 295                 300

Val Leu Lys Lys Glu Val Ser Glu Thr Gln His Gly Thr Ile Leu Ile
305                 310                 315                 320

Lys Val Glu Tyr Lys Gly Glu Asp Ala Pro Cys Lys Ile Pro Phe Ser
                325                 330                 335

Thr Glu Asp Gly Gln Gly Lys Ala His Asn Gly Arg Leu Ile Thr Ala
            340                 345                 350

Asn Pro Val Val Thr Lys Lys Glu Glu Pro Val Asn Ile Glu Ala Glu
        355                 360                 365

Pro Pro Phe Gly Glu Ser Asn Ile Val Ile Gly Ile Gly Asp Lys Ala
    370                 375                 380

Leu Lys Ile Asn Trp Tyr Lys Lys Gly
385                 390
```

<210> SEQ ID NO 4
<211> LENGTH: 395
<212> TYPE: PRT
<213> ORGANISM: Dengue 4

-continued

<400> SEQUENCE: 4

```
Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
            20                  25                  30

Thr Met Ala Gln Gly Lys Pro Thr Leu Asp Phe Glu Leu Ile Lys Thr
        35                  40                  45

Thr Ala Lys Glu Val Ala Leu Leu Arg Thr Tyr Cys Ile Glu Ala Ser
    50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Gln Tyr Ile Cys Arg Arg Asp Val
                85                  90                  95

Val Asp Arg Gly Trp Gly Asn Gly Cys Gly Leu Phe Gly Lys Gly Gly
            100                 105                 110

Val Val Thr Cys Ala Lys Phe Ser Cys Ser Gly Lys Ile Thr Gly Asn
        115                 120                 125

Leu Val Gln Ile Glu Asn Leu Glu Tyr Thr Val Val Val Thr Val His
    130                 135                 140

Asn Gly Asp Thr His Ala Val Gly Asn Asp Thr Ser Asn His Gly Val
145                 150                 155                 160

Thr Ala Thr Ile Thr Pro Arg Ser Pro Ser Val Glu Val Lys Leu Pro
                165                 170                 175

Asp Tyr Gly Glu Leu Thr Leu Asp Cys Glu Pro Arg Ser Gly Ile Asp
            180                 185                 190

Phe Asn Glu Met Ile Leu Met Lys Met Lys Lys Lys Thr Trp Leu Val
        195                 200                 205

His Lys Gln Trp Phe Leu Asp Leu Pro Leu Pro Trp Ala Ala Gly Ala
    210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Thr Gly Ala Thr Glu Val Asp Ser
            260                 265                 270

Gly Asp Gly Asn His Met Tyr Ala Gly His Leu Lys Cys Lys Val Arg
        275                 280                 285

Met Glu Lys Leu Arg Ile Lys Gly Met Ser Tyr Thr Met Cys Ser Gly
    290                 295                 300

Lys Phe Ser Ile Asp Lys Glu Met Ala Glu Thr Gln His Gly Thr Thr
305                 310                 315                 320

Val Val Lys Val Lys Tyr Glu Gly Ala Gly Ala Pro Cys Lys Val Pro
                325                 330                 335

Ile Glu Ile Arg Asp Val Asn Lys Glu Lys Val Val Gly Arg Ile Ile
            340                 345                 350

Ser Ser Thr Pro Phe Ala Glu Tyr Thr Asn Ser Val Thr Asn Ile Glu
        355                 360                 365

Leu Glu Pro Pro Phe Gly Asp Ser Tyr Ile Val Ile Gly Val Gly Asp
    370                 375                 380

Ser Ala Leu Thr Leu His Trp Phe Arg Lys Gly
385                 390                 395
```

<210> SEQ ID NO 5
<211> LENGTH: 451
<212> TYPE: PRT
<213> ORGANISM: Artificial Sequence
<220> FEATURE:
<223> OTHER INFORMATION: DEN4-80EZip

<400> SEQUENCE: 5

```
Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
            20                  25                  30

Thr Met Ala Gln Gly Lys Pro Thr Leu Asp Phe Glu Leu Ile Lys Thr
        35                  40                  45

Thr Ala Lys Glu Val Ala Leu Leu Arg Thr Tyr Cys Ile Glu Ala Ser
    50                  55                  60

Ile Ser Asn Ile Thr Thr Ala Thr Arg Cys Pro Thr Gln Gly Glu Pro
65                  70                  75                  80

Tyr Leu Lys Glu Glu Gln Asp Gln Gln Tyr Ile Cys Arg Arg Asp Val
                85                  90                  95

Val Asp Arg Gly Trp Gly Asn Gly Cys Gly Leu Phe Gly Lys Gly Gly
            100                 105                 110

Val Val Thr Cys Ala Lys Phe Ser Cys Ser Gly Lys Ile Thr Gly Asn
        115                 120                 125

Leu Val Gln Ile Glu Asn Leu Glu Tyr Thr Val Val Val Thr Val His
    130                 135                 140

Asn Gly Asp Thr His Ala Val Gly Asn Asp Thr Ser Asn His Gly Val
145                 150                 155                 160

Thr Ala Thr Ile Thr Pro Arg Ser Pro Ser Val Glu Val Lys Leu Pro
                165                 170                 175

Asp Tyr Gly Glu Leu Thr Leu Asp Cys Glu Pro Arg Ser Gly Ile Asp
            180                 185                 190

Phe Asn Glu Met Ile Leu Met Lys Met Lys Lys Lys Thr Trp Leu Val
        195                 200                 205

His Lys Gln Trp Phe Leu Asp Leu Pro Leu Pro Trp Ala Ala Gly Ala
    210                 215                 220

Asp Thr Ser Glu Val His Trp Asn Tyr Lys Glu Arg Met Val Thr Phe
225                 230                 235                 240

Lys Val Pro His Ala Lys Arg Gln Asp Val Thr Val Leu Gly Ser Gln
                245                 250                 255

Glu Gly Ala Met His Ser Ala Leu Thr Gly Ala Thr Glu Val Asp Ser
            260                 265                 270

Gly Asp Gly Asn His Met Tyr Ala Gly His Leu Lys Cys Lys Val Arg
        275                 280                 285

Met Glu Lys Leu Arg Ile Lys Gly Met Ser Tyr Thr Met Cys Ser Gly
    290                 295                 300

Lys Phe Ser Ile Asp Lys Glu Met Ala Glu Thr Gln His Gly Thr Thr
305                 310                 315                 320

Val Val Lys Val Lys Tyr Glu Gly Ala Gly Ala Pro Cys Lys Val Pro
                325                 330                 335

Ile Glu Ile Arg Asp Val Asn Lys Glu Lys Val Val Gly Arg Ile Ile
            340                 345                 350

Ser Ser Thr Pro Phe Ala Glu Tyr Thr Asn Ser Val Thr Asn Ile Glu
        355                 360                 365

Leu Glu Pro Pro Phe Gly Asp Ser Tyr Ile Val Ile Gly Val Gly Asp
```

-continued

```
    370                 375                 380

Ser Ala Leu Thr Leu His Trp Phe Arg Lys Gly Gly Gly Gly Ser Gly
385                 390                 395                 400

Gly Gly Gly Thr Gly Gly Gly Ser Gly Gly Gly Ser Pro Arg Met Lys
                405                 410                 415

Gln Leu Glu Asp Lys Val Glu Glu Leu Leu Ser Lys Asn Tyr His Leu
            420                 425                 430

Glu Asn Glu Val Ala Arg Leu Lys Lys Leu Val Gly Glu Arg Gly Gly
        435                 440                 445

Cys Gly Gly
    450
```

DENGUE VIRUS VACCINE COMPOSITIONS AND METHODS OF USE THEREOF

CROSS-REFERENCE TO RELATED APPLICATIONS

This application is a § 371 National Phase Application of International Application No. PCT/US2015/066549, filed Dec. 18, 2015, which claims the benefit of U.S. Provisional Application No. 62/095,331, filed Dec. 22, 2014, which is herein incorporated by reference in its entirety.

FIELD OF THE INVENTION

The invention relates to compositions that elicit an immunological response against dengue virus infections, useful for the prevention and/or treatment of dengue virus infections in a subject, and/or the clinical manifestations thereof.

REFERENCE TO SEQUENCE LISTING SUBMITTED ELECTRONICALLY

The sequence listing of the present application is submitted electronically via EFS-Web as an ASCII formatted sequence listing with a file name "23913WOPCTSEQ.TXT", creation date of Nov. 23, 2015, and a size of 17.5 KB. This sequence listing submitted EFS-Web is part of the specification and is herein incorporated by reference in its entirety.

BACKGROUND OF THE INVENTION

The family Flaviviridae includes the prototype yellow fever virus (YF), the four serotypes of dengue virus (DENV-1, DENV-2, DENV-3, and DENV-4), Japanese encephalitis virus (JE), tick-borne encephalitis virus (TBE), West Nile virus (WN), Saint Louis encephalitis virus (SLE), and about 70 other disease causing viruses. Flaviviruses are small, enveloped viruses containing a single, positive-strand RNA genome. Ten gene products are encoded by a single open reading frame and are translated as a polyprotein organized in the order: capsid (C), "preMembrane" (prM, which is processed to "Membrane" (M) just prior to virion release from the cell), "envelope" (E), followed by non-structural (NS) proteins NS1, NS2a, NS2b, NS3, NS4a, NS4b and NS5 (reviewed in Chambers, T. J. et al., *Annual Rev Microbiol* (1990) 44:649-688; Henchal, E. A. and Putnak, J. R., *Clin Microbiol Rev.* (1990) 3:376-396). Individual flaviviral proteins are then produced through precise processing events mediated by the host as well as virally encoded proteases.

The envelope of flaviviruses is derived from the host cell membrane and contains the virally-encoded membrane anchored membrane (M) and envelope (E) glycoproteins. The E glycoprotein is the largest viral structural protein and contains functional domains responsible for cell surface attachment and intra-endosomal fusion activities. It is also a major target of the host immune system, inducing the production of virus neutralizing antibodies, which are associated with protective immunity.

Dengue viruses are transmitted to man by mosquitoes of the genus *Aedes*, primarily *A. aegypti* and *A. albopictus*. Infection by dengue viruses leads to a diverse clinical picture ranging from an inapparent or mild febrile illness, through classical dengue fever (DF), to dengue hemorrhagic fever/dengue shock syndrome (DHF/DSS). Dengue fever is characterized by high fever, headache, joint and muscle pain, rash, lymphadenopathy and leucopenia (Gibbons, R. V. and D. W. Vaughn, *British Medical Journal* (2002) 324: 1563-1566). DHF/DSS is a more severe form of infection more common in children, marked by vascular permeability and/or severe hemorrhagic manifestations ranging from the presence of petechiae and ecchymosis to spontaneous severe hemorrhage and profound shock. Without diagnosis and prompt medical intervention, the sudden onset and rapid progression of DHF/DSS can be fatal if untreated.

Dengue viruses are the most significant group of arthropod-transmitted viruses in terms of global morbidity and mortality with an estimated one hundred million dengue infections occurring annually including at least 36 million cases of dengue fever and 250,000 to 500,000 cases of DHF/DSS (Gubler, D. J., *Clin. Microbiol. Rev.* (1998) 11:480-496; Gibbons, supra). With the global increase in population, urbanization of the population especially throughout the tropics, and the lack of sustained mosquito control measures, the mosquito vectors of dengue have expanded their distribution throughout the tropics, subtropics, and some temperate areas, bringing the risk of dengue infection to over half the world's population. Modern jet travel and human emigration have facilitated global distribution of dengue serotypes, such that multiple serotypes of dengue are now endemic in many regions. There has been an increase in the frequency of dengue epidemics and the incidence of DHF/DSS in the last 20 or more years. For example, in Southeast Asia, DHF/DSS is a leading cause of hospitalization and death among children (Gubler, supra; Gibbons and Vaughn, supra).

To date, the development of flavivirus vaccines has been met with mixed success. There are four basic approaches that have been implemented in an effort to produce vaccine candidates to protect against disease caused by flaviviruses: live-attenuated, inactivated whole virus, recombinant subunit protein, and DNA-based vaccines. A live-attenuated vaccine for yellow fever virus has been available for decades and more recently a live attenuated vaccine for Japanese encephalitis has been registered in various countries around the world. The use of inactivated whole virus vaccines has been demonstrated for TBE and JE viruses with several registered products available. Heinz et al. Flavivirus and flavivirus vaccines. *Vaccine* 30: 4301-06 (2012).

Despite the successes of the YF, JE, and TBE vaccines highlighted above, the use of live-attenuated virus and inactivated virus methods to develop vaccines for dengue virus has been met with significant challenges. There are four serotypes of dengue virus (DENV1, DENV2, DENV3, and DENV4) and strains of each serotype are found circulating throughout the dengue endemic regions of the world. Natural infection confers long lasting immunity to the infecting serotype but not to other dengue serotypes. The more severe forms of the disease (DHF/DSS) occur most often after secondary dengue infection, when infection with one serotype of dengue virus is followed by a second infection with another serotype. The more frequent association of DHF and DSS with secondary dengue infection has been hypothesized to be due to non-neutralizing antibodies induced by infection with one virus type enhancing infectivity of a second dengue virus type (antibody-dependent enhancement—ADE).

To date, the majority of the vaccines tested clinically are live, attenuated vaccines. The use of non-replicating vaccine candidates is also being explored. For example, Ivy et al. (U.S. Pat. No. 6,432,411) disclose a tetravalent subunit vaccine comprising DEN1-4 80% E (the peptide region of DEN1-4 corresponding to amino acids 1-395 of the DENV-2 envelope polypeptide) proteins. Ivy et al, supra, also report compositions comprising DENV 1-4 80% E and ISCOMATRIX® adjuvant. Coller et al. (WO 2012/154202) disclose tetravalent formulations comprising DEN1-4 80% E of DEN 1-4. Inactivated viruses may also be used as potential vaccine candidates or as components of an effective vaccine (Putnak et al. *Vaccine* 23: 4442-4452 (2005), U.S. Pat. Nos. 6,190,859, 6,254,873 and Sterner et al. WO 2007/002470). Compositions comprising a live attenuated dengue virus vaccine and a non-replicating dengue vaccine are disclosed in International Patent Application No. PCT/US14/042625 (WO/2014/204892).

However, despite prior efforts to develop a dengue vaccine, to date no dengue vaccine is currently registered. Thus, there remains a need for a stable, safe, and effective vaccine that can induce a protective immune response against dengue infection and/or dengue-related disease.

SUMMARY OF THE INVENTION

The present invention relates to a dengue virus vaccine composition comprising a pharmaceutically effective amount of (a) a live attenuated dengue vaccine comprising at least one live attenuated dengue virus (LAV) or at least one live attenuated chimeric flavivirus (LACV), wherein the LAV and the LACV comprise a viral genome that contains a deletion of about 30 nucleotides corresponding to the TL-2 stem-loop structure of the 3' untranslated (UTR) region; which reduces the replicative capacity of the virus, and (b) a non-replicating dengue vaccine. The presence of the non-replicating dengue vaccine in the same composition as the live attenuated vaccine was found to not significantly impact live virus viability, thereby permitting the live and non-replicating vaccine to be administered in the same formulation ("co-formulation").

In some embodiments, the non-replicating dengue vaccine is selected from a recombinant dengue subunit vaccine, a DNA vaccine, a conjugate vaccine, or an inactivated dengue vaccine. In further embodiments, the non-replicating dengue vaccine is either a recombinant dengue subunit vaccine or an inactivated dengue vaccine. In some embodiments of the invention, the non-replicating dengue vaccine is a recombinant dengue subunit vaccine which comprises at least one dengue envelope (E) protein or fragment thereof. In preferred embodiments of the invention, the recombinant dengue subunit vaccine is tetravalent and comprises truncated dengue E proteins which each consist of about 80% of the length of wild type E of dengue virus ("DENV", alternatively "DEN") serotype 1, a.k.a. DENV 1, DENV 2, DENV 3 and DENV 4, starting from amino acid residue 1 at its N-terminus.

In additional embodiments of the invention, the live attenuated dengue vaccine is a tetravalent LAV or "LATV" (i.e. comprises live attenuated dengue viruses from DENV 1-4, or live attenuated chimeric flaviviruses from DENV 1-4, as defined herein, or a combination thereof, wherein at least one of the LAVs or LACVs is a Δ30LAV or a Δ30LACV). In additional embodiments of the invention, the live attenuated dengue vaccine is tetravalent and comprises at least one chimeric flavivirus; wherein the chimeric flavivirus comprises a viral genome that contains nucleotide sequences encoding the prM and E proteins of a single dengue virus serotype and nucleotide sequences encoding the capsid and non-structural proteins of a different flavivirus, wherein the chimeric flavivirus is attenuated. In some embodiments of the invention, the capsid and nonstructural proteins of the chimeric flavivirus is from a different dengue serotype than the prM and E proteins.

In a preferred embodiments of the invention, the live attenuated dengue vaccine is a live attenuated tetravalent vaccine comprising a DEN1Δ30 virus, a DEN2/4Δ30 virus (a DEN2Δ30LACV on a DEN4 backbone), a DEN3Δ30 virus and a DEN4Δ30 virus. See FIG. 1.

The invention also relates to dengue virus vaccine compositions that comprise a live attenuated dengue vaccine, a recombinant dengue subunit vaccine and an adjuvant, wherein the live attenuated dengue vaccine comprises at least one Δ30LAV or Δ30LACV. In some embodiments described herein, the adjuvant is an aluminum salt adjuvant. In alternative embodiments, the adjuvant is a saponin-based adjuvant or a toll-like receptor agonist adjuvant.

Other aspects of this invention include methods of preventing dengue infection, or preventing or ameliorating the symptoms thereof, comprising administering a pharmaceutically effective amount of the dengue virus vaccine compositions of the invention to a patient in need thereof. In additional embodiments of this aspect of the invention, the compositions are administered in a prime/boost regime, wherein a first dose of the composition is administered to a patient in need thereof, a predetermined amount of time is allowed to pass, and a second dose of the composition is administered to the patient. Additional doses may optionally be administered to the patient after a predetermined amount of time has passed between each dose.

In additional embodiments, the invention relates to a method of inducing an immune response against dengue infection, thereby reducing the likelihood of dengue infection, comprising the steps of:

(a) mixing a first dengue vaccine and a second dengue vaccine, to form a dengue virus vaccine composition,
  wherein the first dengue vaccine is a live attenuated tetravalent dengue vaccine comprising live attenuated viruses (LAV) of dengue serotypes 1-4, or live attenuated chimeric flaviviruses (LACV) that are immunogenic against dengue serotypes 1-4, or a combination thereof, wherein at least one LAV or LACV is a Δ30LAV or a Δ30LACV;
  wherein the second dengue vaccine is a recombinant tetravalent dengue subunit vaccine or an inactivated tetravalent dengue vaccine; and wherein the recombinant tetravalent dengue subunit vaccine comprises dengue envelope (E) proteins of dengue serotypes 1-4 or fragments thereof;

(b) administering the dengue virus vaccine composition of step (a) after mixing to a patient in which an immune response against dengue is to be induced, thereby reducing the likelihood of dengue infection. In some embodiments of the method of the invention, the immune response prevents dengue infection or prevents or ameliorates the symptoms thereof. In additional embodiments of the invention, a second dose of the composition is administered to the patient after a predetermined amount of time is allowed to pass. The first dengue vaccine and the second dengue vaccine of the second dose of the composition can be formulated in a single vial or in two separate vials and mixed together prior to administration to the patient.

The invention also relates to the use of the dengue virus vaccine compositions of the invention for the treatment or prophylaxis of disease associated with dengue infection, such as dengue fever, DSS or DHF.

As used throughout the specification and in the appended claims, the singular forms "a," "an," and "the" include the plural reference unless the context clearly dictates otherwise.

Reference to "or" indicates either or both possibilities unless the context clearly dictates one of the indicated possibilities. In some cases, "and/or" was employed to highlight either or both possibilities.

As used throughout the specification and appended claims, the following definitions and abbreviations apply:

The term "live attenuated virus," also referred to as "LAV" herein, means a live attenuated dengue virus, wherein the ability of the virus to cause disease is reduced compared to wild-type dengue virus.

The term "live attenuated chimeric virus" (alternatively "live attenuated chimeric flavivirus") or "LACV" refers to a live attenuated chimeric virus wherein the viral genome comprises a backbone of a first flavivirus (including C, NS1, NS2A, NS2B, NS3, NS4A, NS4B and NS5 genes) and the preMembrane (prM) and envelope (E) genes of a second flavivirus, wherein the second flavivirus is selected from DENV1, DENV2, DENV3 or DENV4. The first flavivirus can be a different dengue serotype or another flavivirus, such as yellow fever virus.

The term "Δ30 LAV" refers to a live attenuated DEN1, DEN2, DEN3, or DEN4 virus, wherein the LAV comprises a viral genome that contains a deletion of about 30 nucleotides (nt) corresponding to the TL2 stem-loop structure of the 3' untranslated (UTR) region from about nt 143 to about nt 172, which reduces the replicative capacity of the virus (see WO 03/092592).

The term "Δ30 LACV" refers to a live attenuated chimeric flavivirus (LACV) from DENV 1-4 wherein the LACV comprises a viral genome that contains a deletion of about 30 nt corresponding to the TL2 stem-loop structure of the 3' UTR region from about nt 143 to about nt 172, which reduces the replicative capacity of the virus (see WO 03/092592).

The term "Δ30/Δ31 LAV" refers to a live attenuated DEN1, DEN2, DEN3, or DEN4 virus, wherein the viral genome comprises a deletion of about 30 nt of the TL2 stem-loop structure of the 3' UTR, and further comprises a separate, noncontiguous, upstream deletion of about 31 nt of the 3' UTR which removes sequence up to and including the TL-3 homologous structure so that the deletion extends as far as the 5' boundary of the TL-3 homologous structure of the dengue 3'UTR. See Whitehead et al., U.S. Pat. No. 8,337,860. In preferred embodiments of the invention, the DEN3 LAV comprises the Δ30/Δ31 mutations.

The term "Δ30/Δ31 LACV" refers to a live attenuated chimeric DEN1, DEN2, DEN3, or DEN4 virus as described above, wherein the viral genome of the chimeric virus comprises a 30 nt deletion of the TL2 stem-loop structure of the 3' UTR, and further comprises a separate, noncontiguous, upstream 31 nt deletion of the 3' UTR, which deletes the TL-3 structure, as described above.

The term "LATV" or "live attenuated tetravalent virus" or "LATV vaccine" refers to a vaccine comprising an effective amount of a DEN1 LAV or LACV, a DEN2 LAV or LACV, a DEN3 LAV or LACV and a DEN4 LAV or LACV, wherein at least one of the dengue LAVs or LACVs comprises the Δ30 mutation of the TL-2 structure in the 3' UTR, as described above and in WO 03/092592. In some preferred embodiments, the LATV comprises the following features: (1) rDEN1Δ30, which is a DENV1 LAV wherein the DENV1 viral genome comprises a 30 nt deletion corresponding to the TL2 stem-loop structure in the 3' UTR; (2) rDEN2/4Δ30, which is a DENV2 LACV comprising the DENV2 prM and E genes on a DENV4 backbone, wherein the DEN4 backbone comprises a 30-nt deletion corresponding to the TL2 stem-loop structure in the 3' UTR; (3) rDEN3Δ30/Δ31, which is a DENV3 LAV wherein the DENV3 viral genome comprises a 30 nt deletion corresponding to the TL2 stem-loop structure in the 3' UTR and a separate, noncontiguous, upstream 31 nt deletion corresponding to the TL-3 structure of the 3' UTR; and (4) rDEN4Δ30, which is a DENV4 LAV wherein the DENV4 viral genome comprises a 30 nt deletion corresponding to the TL2 stem-loop structure in the 3' UTR (see FIG. 1).

"Non-replicating vaccine" refers to a dengue virus vaccine for the prevention or treatment of dengue virus infection or the clinical symptoms thereof, selected from a recombinant subunit vaccine, an inactivated vaccine, a conjugate vaccine, or a DNA vaccine.

"Inactivated vaccine" refers to a vaccine comprising an effective amount of a killed or inactive whole dengue virus and a pharmaceutically acceptable carrier, wherein the virus is inactivated by any means, including with chemicals, heat or radiation. An inactivated vaccine has a low residual infectivity following inactivation, e.g. <5 plaque forming units (PFU's)/mL after inactivation. In preferred embodiments, there is very low amount of residual infectivity following inactivation, e.g. ≤4 PFU's/mL, ≤3 PFU's/mL, or ≤2 PFU's/mL, <1 PFU/mL, ≤0.5 PFU/mL, or ≤0.1 PFU/mL. The PFU's of a particular vaccine may be determined, for example, by using a plaque assay, an immunostaining assay, or other method known in the art for detecting viral infectivity.

"Conjugate vaccine" refers to a vaccine comprising a dengue antigen covalently attached to a carrier protein.

A "DNA vaccine" is a vaccine comprising a sequence of nucleotides that encodes a dengue protein antigen, including dengue proteins, dengue protein fragments, and dengue fusion proteins, and variants thereof. DNA vaccines comprise a plasmid (e.g. a DNA or viral plasmid) comprising a sequence of nucleotides that encode an antigen of interest, operably linked to a promoter.

"Subunit vaccine" refers to a vaccine that includes one or more dengue antigen components, but not complete dengue viruses, such as dengue immunogenic epitopes, dengue proteins, dengue antigen fusion proteins, including fusions of different dengue serotype antigens, or dengue protein fragments. Subunit vaccines, as used herein, can be monovalent (comprise a single dengue antigen) or multivalent (comprise more than one antigen component). In preferred embodiments, the subunit vaccine is tetravalent.

The term "co-formulation prime-boost" refers to a therapeutic regimen comprising (1) administration to a patient in need thereof a dengue virus vaccine composition, wherein the composition comprises (a) at least one live attenuated dengue virus (LAV) or live attenuated chimeric flavivirus (LACV), wherein the LAV or LACV comprises a Δ30 mutation in the 3' untranslated region of the viral genome and wherein the viral genome of the LACV comprises the prM and E genes of a single dengue virus serotype and the C and non-structural genes of a different flavivirus, (b) a non-replicating dengue vaccine, and (c) a pharmaceutically acceptable carrier; (2) waiting for a predetermined amount of time to pass; and (3) administration to the patient of a second dengue virus vaccine composition, as described above. In some embodiments, the non-replicating dengue vaccine is a subunit vaccine or an inactivated vaccine. The second dengue virus vaccine composition can be the same or different from the first dengue virus vaccine composition, as long as it comprises a live attenuated dengue vaccine and a non-replicating dengue vaccine in accordance with the invention. The dengue virus vaccines used in the compositions of the invention are useful for inducing a virus neutralizing antibody response to the homologous dengue viruses in human patients.

The term “treatment” refers to both therapeutic treatment and prophylactic or preventative measures. Individuals or patients “in need of” treatment include those already with a dengue infection, whether or not manifesting any clinical symptoms, as well as those at risk of being infected with dengue. Treatment of a patient with the dengue vaccine compositions or co-formulations of the invention includes one or more of the following: inducing/increasing an immune response against dengue in the patient, inducing a virus neutralizing antibody response against one or more dengue viruses, preventing, ameliorating, abrogating, or reducing the likelihood of the clinical manifestations of dengue in patients who have been infected with dengue, preventing or reducing the likelihood of developing dengue fever, DHF, or DSS and/or other disease or complication associated with dengue infection, reducing the severity or duration of the clinical symptoms of dengue infection and/or other disease or complication associated with dengue, and preventing or reducing the likelihood of dengue infection.

The term “pharmaceutically effective amount” or “effective amount” means sufficient vaccine composition is introduced to a patient to produce a desired effect, including, but not limited to: inducing/increasing an immune response against dengue in the patient, inducing/increasing a virus neutralizing antibody response against dengue in a patient, preventing or reducing the likelihood of dengue infection, preventing or reducing the likelihood of dengue recurrent infection, preventing, ameliorating or abrogating the clinical manifestations of dengue infection in patients who have been infected with dengue, preventing dengue fever, DHF and/or DSS, or reducing the severity or duration of disease associated with dengue. One skilled in the art recognizes that this level may vary.

The term “immune response” refers to a cell-mediated (T-cell) immune response and/or an antibody (B-cell) response.

The term “patient” refers to a mammal capable of being infected with a dengue virus, such as DEN1, DEN2, DEN3, or DEN4, that is to receive the dengue vaccine compositions/co-formulations described herein, including both immunocompetent and immunocompromised individuals. In preferred embodiments, the patient is a human. As defined herein, a “patient” includes those already infected with dengue, either through natural infection or vaccination or those that may subsequently be exposed.

“MAA” means Merck aluminum adjuvant. MAA is an amorphous aluminum hydroxyphosphate sulfate adjuvant.

An “ISCOM-like adjuvant” is an adjuvant comprising an immune stimulating complex (ISCOM), which is comprised of a saponin, cholesterol, and a phospholipid, which together form a characteristic caged-like particle, having a unique spherical, caged-like structure that contributes to its function (for review, see Barr and Mitchell, *Immunology and Cell Biology* 74: 8-25 (1996)). This term includes both ISCOM™ adjuvants, which are produced with an antigen and comprise antigen within the ISCOM™ particle and ISCOM™ matrix adjuvants, which are hollow ISCOM-type adjuvants that are produced without antigen. In preferred embodiments of the compositions and methods provided herein, the ISCOM-type adjuvant is an ISCOM™ matrix particle adjuvant, such as ISCOMATRIX™, which is manufactured without antigen (ISCOM™ and ISCOMATRIX™ are registered trademarks of CSL Limited, Parkville, Australia).

The designation “rDEN1Δ30-1545” refers to a recombinant dengue 1 virus wherein the viral genome comprises (1) a 30 nt deletion of the TL2 stem-loop structure of the 3' UTR and (2) a substitution at nucleotide position 1545, which occurred after adaptation of the virus to growth in Vero cells.

The designation “rDEN2/4 Δ 30(ME)-1495,7163” refers to a recombinant chimeric dengue 2/4 virus, wherein the viral genome comprises: (1) a dengue 4 backbone (C, NS1, NS2A, NS2B, NS3, NS4A, NS4B, NS5 genes) comprising (i) a 30 nt deletion of the TL2 stem-loop structure of the 3' UTR, and (ii) substitutions at nucleotide positions 1495 and 7163, which occurred after adaptation of the virus to growth in Vero cells, and (2) dengue 2 prM and E genes.

The designation “rDEN3Δ30/31-7164” refers to a recombinant dengue 3 virus wherein the viral genome comprises: (1) a 30 nt deletion of the TL2 stem-loop structure of the 3' UTR, (2) a separate, 31 nt deletion in the 3'UTR, upstream of the Δ30 mutation, that deletes the TL-3 structure and (3) a substitution at nucleotide position 7164, which occurred after adaptation of the virus to growth in Vero cells.

The designation “rDEN4Δ 30-7132,7163,8308” refers to a recombinant dengue 4 virus wherein the viral genome comprises: (1) a 30 nt deletion of the TL2 stem-loop structure of the 3' UTR and (2) substitutions at nucleotide position 7132, 7163 and 8308, which occurred after adaptation of the virus to growth in Vero cells.

“V180” refers to a tetravalent subunit vaccine comprised of truncated envelope glycoproteins (DEN-80E) from each of the 4 dengue virus serotypes (DENV1, DENV2, DENV3, and DENV4), wherein the E proteins each constitute approximately 80% of the length of wild type E starting from amino acid residue 1 at its N-terminus, such that said E protein is secretable into growth medium when expressed recombinantly in a host cell. See Coller et al. WO 2012/154202.

The following abbreviations are used herein and have the following meanings: C is the dengue capsid gene, DEN (alternatively DENV) is dengue virus, DF is dengue fever, DHF is dengue hemorrhagic fever, DSS is dengue shock syndrome, h is hours, GMT is geometric mean titer, IM is intramuscular, IMX is Iscomatrix™, JE is Japanese encephalitis, LAV is live attenuated virus, MAA is Merck aluminum adjuvant, MAPA is Merck aluminum phosphate adjuvant, NS (used in NS1-NS5) is non-structural, nt is nucleotide, PFU is plaque forming units, prM is the dengue preMembrane gene, SC is subcutaneous, TBE is tick-borne encephalitis, UTR is untranslated region, WN (alternatively WNV) is West Nile Virus, YF (alternatively YFV) is yellow fever virus, and wt is wild type.

BRIEF DESCRIPTION OF THE DRAWINGS

FIG. 3 provides the dengue serotype neutralizing antibody titers (LiCor$_{50}$ GMT) induced in Rhesus Macaques at week 4 (4 weeks post-dose 1, see Example 3). The immunization schedule and formulations used in the study are shown in Table 2. Immunization titers were determined using a LiCor-based microneutralization assay as described in Example 3.

FIG. 4 provides the dengue serotype neutralizing antibody titers (LiCor$_{50}$ GMT) induced in the same Rhesus Macaques for which data is provided in FIG. 3 at week 20 (4 weeks post-dose 2, see Example 3).

FIG. 6 provides the dengue serotype neutralizing antibody titers (LiCor$_{50}$ GMT) induced in Rhesus Macaques at week 4 (4 weeks post-dose 1, see Example 4). The immunization schedule and formulations used in the study are shown in Table 3. Immunization titers were determined using a LiCor-based microneutralization assay as described in Example 3.

FIG. 7 provides the dengue serotype neutralizing antibody titers (LiCor$_{50}$ GMT) induced in the same Rhesus Macaques for which data is provided in FIG. 6 at week 28 (4 weeks post-dose 2, see Example 4).

DETAILED DESCRIPTION OF THE INVENTION

Figure 1:
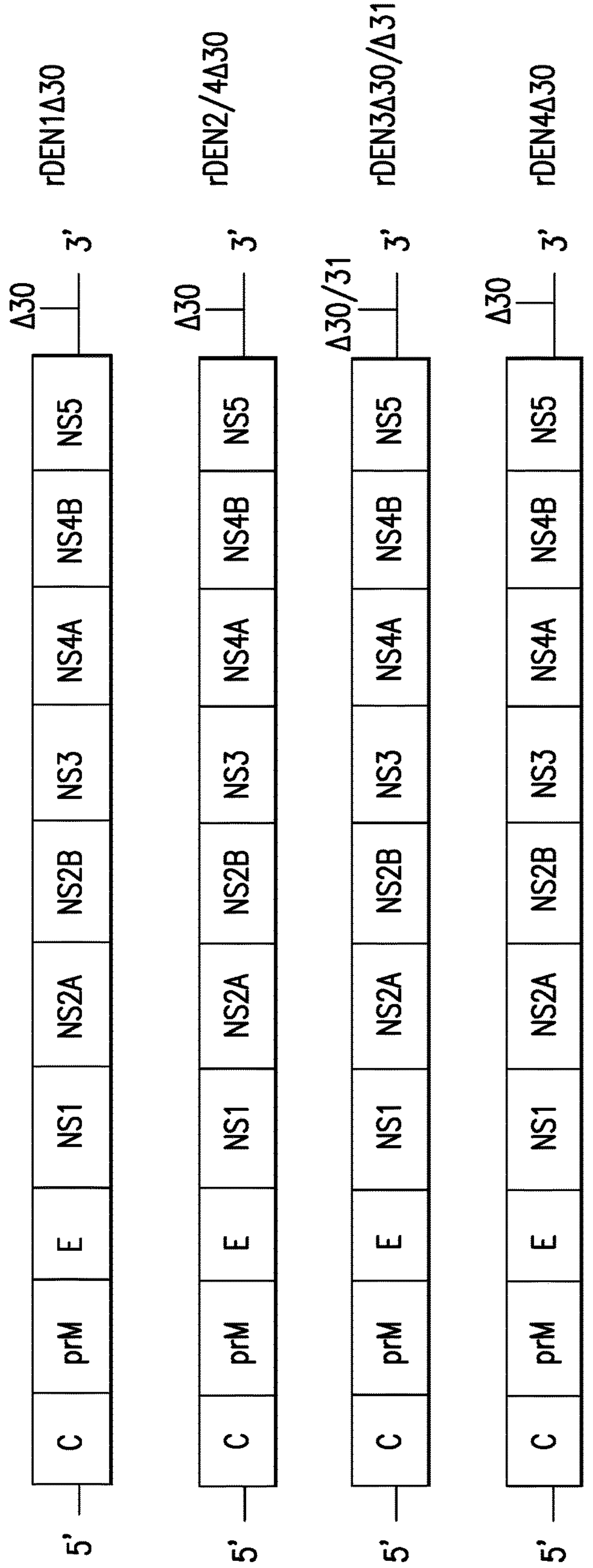
FIG. 1 provides a schematic illustration of the composition of the Δ30 LATV (Δ30 tetravalent live attenuated dengue virus vaccine) used in Examples 1-3.

The present invention relates to a dengue virus vaccine composition comprising a pharmaceutically effective amount of (a) a live attenuated dengue vaccine comprising at least one live attenuated dengue virus (LAV) or at least one live attenuated chimeric flavivirus (LACV), wherein the LAV and the LACV comprise a viral genome that contains a deletion of about 30 nucleotides corresponding to the TL-2 stem-loop structure of the 3' untranslated (UTR) region that reduces the replicative capacity of the virus, and wherein the viral genome of the LACV comprises a sequence of nucleotides that encodes the prM and E proteins of a single dengue serotype and nucleotide sequences encoding the C and non-structural proteins of a different flavivirus; and (b) a non-replicating dengue vaccine, optionally further comprising an adjuvant. The LAV or LACV and the second vaccine are formulated in the same vial or separate vials and mixed together prior to administration to the subject. In embodiments of the invention, a composition in accordance with the invention is administered to a patient two or more times in a prime-boost treatment regime.

A conventional heterologous prime-boost regime comprising administration of the live attenuated vaccine at one point in time, followed by administration of a non-replicating dengue vaccine from 2 weeks to 2 years later is an alternative approach that can be used, but this approach may cause confusion regarding which vaccine (live attenuated vaccine or non-replicating vaccine) should be administered first in the series. Administration of the live attenuated vaccine and the non-replicating vaccine in the proper order is important because reversal of the order (subunit or inactivated vaccine first, followed by live attenuated vaccine) could lead to an inferior immune response which may increase the person's risk for more severe dengue disease if they were to become naturally infected. Thus, co-administration of the live attenuated vaccine and the non-replicating vaccine to a patient simplifies administration of the complete treatment regime. It is thought that, when administered in a prime-boost regime, the co-formulation of (1) the live attenuated, vaccine and (2) the non-replicating, vaccine will elicit strong immune responses that are primarily driven by the live vaccine at the prime and by the non-replicating vaccine at the boost.

Prior to the present invention, it was thought that the presence of subunit antigen or inactivated vaccine and/or adjuvant in a dengue vaccine composition comprising a live attenuated virus had the potential of inactivating the live attenuated virus resulting in decreased viral titer. Minke et al. (*Vaccine* 29 (2011) 4608-4612 and *Veterinary Immunol. and Immunopathol.* 111 (2006) 47-57) and Guthrie et al. (*Vaccine* 27 (2009) 4434-4438) reported a modified live recombinant canary pox virus expressing the prM/E genes derived from WNV formulated in carbomer adjuvant. However, this vaccine composition did not contain separate viral subunit antigens.

The use of different dengue virus vaccines in prime-boost strategies have been tested. Simmons et al. (*Virology* 396 280-288 (2010); U.S. Pat. Nos. 8,440,202 and 8,241,638) tested a prime boost approach for dengue in rhesus macaques by priming the animals with a non-replicating vaccine in the form of either an inactivated vaccine or a DNA-based vaccine, followed by boosting with a tetravalent live attenuated vaccine. Kanakatte et al. (WO 2008127307) also describe a heterologous prime boost regimen against dengue with the priming immunogen comprising a DNA expression system, an adenovirus expression vector or a Venezuelan equine encephalitis virus replicon system and the boosting immunogen comprising a tetravalent live attenuated vaccine. In this method, the boosting immunogen is administered between two weeks and 2 months of administration of the priming immunogen.

Guy et al. (WO 2008/047023) report a method for inducing protection against DEN1-4 in a patient, comprising: administering (a) a first series of administrations (i) of a dose of a vaccinal dengue virus of a first serotype and of a dose of a vaccinal dengue virus of a second serotype, and (ii) of a dose of a vaccinal dengue virus of a third serotype and of a dose of a vaccinal dengue virus of a fourth serotype, and (b) a second series of administrations of doses (i) and (ii), in which the doses (i) and (ii) are administered simultaneously at separate anatomical sites, and in which the second series is implemented at least 30 days to at most 12 months after the first series. Thus previous reports of prime/boost approaches against dengue focus on the use of the LAV as the boosting immunogen and require that a period of time, from weeks to months passes between administration of the priming composition and administration of the LAV.

We have shown herein that, surprisingly, geometric mean neutralization titers measured in rhesus monkeys that were immunized with the compositions (co-formulations) of the invention (Δ30 LATV+V180) at four weeks post dose 1 were comparable to those induced when the Δ30 LATV vaccine was given alone (see Example 3). This indicates that the co-formulation of the Δ30 LATV vaccine with the V180 subunit vaccine and Alhydrogel® adjuvant does not negatively impact the response to the first dose of live attenuated virus vaccine.

It was further shown herein that both the conventional prime boost (Δ30 LATV prime followed by V180 boost) and the co-formulation prime boost approaches (Δ30 LATV+V180 co-formulation prime followed by Δ30 LATV+V180 co-formulation boost) induced superior neutralization titers to all four DENV types compared to the Δ30 LATV vaccine alone. Neutralization responses in the coformulation group at four weeks following the booster dose were equivalent to, if not better, than those induced in the groups receiving the conventional prime-boost regimen. This indicates that the coformulation of the Δ30 LATV vaccine with the V180 subunit vaccine and Alhydrogel® adjuvant does not negatively impact the response to the subunit boost.

Thus, the benefits of a heterologous prime/boost approach may be achieved through (a) administration of a first dengue vaccine composition to a patient in need thereof, the composition comprising: (1) a live attenuated dengue vaccine, wherein the live attenuated dengue vaccine comprises at least one LAV or LACV comprising a viral genome, wherein the viral genome comprises a deletion of about 30-nucleotides corresponding to the TL-2 stem-loop structure in the 3' UTR, and (2) a non-replicating dengue vaccine; (b) allowing a predetermined amount of time to pass; and (3) administration of a second dengue virus vaccine composition to the patient. In some embodiments of the invention, the non-replicating vaccine is selected from a subunit dengue vaccine and an inactivated dengue vaccine. In this embodiment, the dengue vaccine composition of the invention is administered to the patient as both the priming and the boosting composition. In embodiments of the invention, the first dengue vaccine composition and the second dengue vaccine composition are the same. In alternative embodiments, the first dengue vaccine composition and the second dengue vaccine composition are different.

Accordingly, the invention relates to a method of preventing or reducing the likelihood of dengue infection, or preventing, treating, or ameliorating the clinical manifestations thereof, the method comprising:

(a) administering a first dengue virus vaccine composition to a patient in need thereof,
(b) waiting for a predetermined amount of time to pass after step (a); and
(c) administering to the patient a second dengue virus vaccine composition, wherein the first and second dengue virus vaccine composition comprise:
  (i) a live attenuated dengue vaccine comprising at least one live attenuated dengue virus (LAV) or live attenuated chimeric flavivirus (LACV), wherein the LACV comprises the prM and E genes of a single dengue virus serotype and the backbone of a different flavivirus; and wherein the LAV or LACV comprise a viral genome that comprises a 30-nucleotide deletion of the TL-2 stem-loop structure in the 3'UTR; and
  (ii) a non-replicating dengue vaccine.

In some embodiments of the method above, the non-replicating vaccine is a dengue subunit vaccine or an inactivated dengue vaccine.

In preferred embodiments of the invention, the live attenuated and the non-replicating dengue vaccines are tetravalent (i.e. comprise DEN1, DEN2, DEN3, and DEN4 components or induce an immune response against DEN1, DEN2, DEN3, and DEN4).

In some embodiments of the co-formulation prime-boost methods, the second dengue virus vaccine composition of step (c) is the same as the first dengue virus vaccine composition of step (a). In alternative embodiments, the composition of step (c) is not the same as the composition of step (a). In additional embodiments, the method comprises repeating steps (b) and (c) one or more times. In some embodiments, the first vaccine and the second dengue vaccine of step (a) and/or step (c) are formulated in separate vials and mixed together prior to administration. It is thought that the use of the compositions of the invention in a prime/boost regime will elicit strong immune responses that are primarily driven by the live attenuated vaccine at the prime (first dose) and by the non-replicating (e.g. subunit or inactivated vaccine) at the boost (second dose).

Accordingly, the present invention relates to a dengue virus vaccine composition comprising effective amounts of a live attenuated dengue vaccine and a non-replicating dengue vaccine and a pharmaceutically acceptable carrier, wherein the live, attenuated dengue vaccine comprises at least one live attenuated dengue virus (LAV) or at least one live attenuated chimeric flavivirus (LACV), wherein the LAV or LACV comprise a viral genome that comprises a 30-nucleotide deletion of the TL-2 stem-loop structure in the 3'UTR. In some embodiments of the invention, the non-replicating dengue vaccine of the dengue virus vaccine compositions of the invention are selected from a recombinant dengue subunit vaccine or an inactivated dengue vaccine.

To prepare pharmaceutical or sterile dengue virus vaccine compositions of the invention, a live attenuated dengue vaccine and a non-replicating dengue vaccine, as described herein, are admixed with a pharmaceutically acceptable carrier or excipient. Alternatively, a live attenuated dengue vaccine and a non-replicating dengue vaccine comprise a pharmaceutically acceptable carrier prior to mixing and no additional carrier is required when the vaccines are mixed. See, e.g., *Remington's Pharmaceutical Sciences* and *U.S. Pharmacopeia: National Formulary*, Mack Publishing Company, Easton, Pa. (1984). Pharmaceutically acceptable carriers include any and all solvents, dispersion media, isotonic and absorption delaying agents, and the like that are physiologically compatible. The carriers can be suitable for intravenous, intramuscular, subcutaneous, parenteral, rectal, spinal, or epidermal administration (e.g., by injection or infusion).

As used herein, the term "pharmaceutically acceptable carrier" refers to a substance, as described above, which is admixed with an active ingredient (e.g. whole, inactivated virus, live attenuated virus, live attenuated chimeric virus, viral protein, plasmid comprising a sequence of nucleotides encoding a dengue antigen protein, or dengue antigen conjugate) of the invention that is suitable for administration to humans. In embodiments of the invention, the pharmaceutically acceptable carrier does not occur in nature in the same form, e.g. the substance is man-made, either because it does not exist in nature or the purity and/or sterility of the substance is not the same as the corresponding natural substance. For example, sterile water for injection, which is a sterile, bacteria-free, solute-free preparation of distilled water for injection, does not occur in nature in the same form and is considered a pharmaceutically acceptable carrier. In some embodiments, the pharmaceutical compositions of the invention comprise one or more active ingredients disclosed herein (e.g. a tetravalent LAV) and sterile water for injection. In further embodiments, the pharmaceutically acceptable carrier may be another form of water that is appropriate for pharmaceutical or biological preparations and is not the same as water that occurs in nature, including purified water, water for injection, sterile purified water, and bacteriostatic water for injection.

Pharmaceutical compositions typically should be sterile and stable under the conditions of manufacture and storage. Formulations of therapeutic and diagnostic agents may be prepared by mixing with acceptable carriers, excipients, or stabilizers in the form of, e.g., lyophilized powders, slurries, aqueous solutions, suspensions, microemulsions, dispersions, liposomes, or other ordered structure suitable for vaccine formulation and administration (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, N Y; Lieberman, et al. (eds.) (1990) *Pharmaceutical Dosage Forms: Tablets*, Marcel Dekker, N Y; Lieberman, et al. (eds.) (1990) *Pharmaceutical Dosage Forms: Disperse Systems*, Marcel Dekker, N Y; Weiner and Kotkoskie (2000) *Excipient Toxicity and Safety*, Marcel Dekker, Inc., New York, N.Y.).

The dengue virus vaccine co-formulations of the present invention may further comprise additional components including, but not limited to adjuvants, as discussed infra, buffers, stabilizers, solubilizers, salt, anti-microbial preservatives, surfactants, tonicity modifiers, chelating agents, dextran, dextran sulfate, dextran T40, diethanolamine, guanidine, calcium chloride, sodium citrate, albumin, gelatin, polyethylene glycol (PEG), lipids, and heparin. One of skill in the art is readily able to determine which additional excipients should be included in a desired dengue virus vaccine composition or coformulation, dependent on its function in the formulation, as well as the projected mode of administration, dosage, and other factors such as the expected storage time and temperature of the composition. One of skill in the art recognizes that the amount of the additional excipients may vary, and can readily determine a proper amount that is both safe for administration to humans and effective for the desired function.

Live Attenuated Dengue Virus Vaccine

As stated above, the dengue virus vaccine compositions of the invention comprise a live attenuated dengue vaccine comprising at least one LAV, selected from the group consisting of dengue virus type 1 (DEN1), dengue virus type 2 (DEN2), dengue virus type 3 (DEN3) and dengue virus type 4 (DEN4), or LACV, wherein the LAV or LACV comprises a viral genome that comprises a TL-2 Δ30 modification in the 3'UTR, and wherein the LAV or LACV: induces an immune response against dengue, induces a virus neutralizing antibody response against dengue, protects against or reduces the likelihood of infection or reduces the severity or duration of the clinical manifestations thereof. In embodiments of the invention, the live attenuated dengue vaccine is monovalent, bivalent, trivalent or tetravalent, i.e. induces an immune response against or protects against one, two, three or four of DEN serotypes 1-4, respectively. In preferred embodiments of the invention, the live attenuated dengue vaccine is tetravalent, i.e. induces an immune response against or protects against DEN serotypes 1-4 and comprises a DEN1, a DEN2, a DEN3 and a DEN4 component, wherein each component is either an LAV or an LACV.

In some embodiments of the invention, each LAV or LACV component of a LATV of the invention comprises a live attenuated virus which is independently either an attenuated chimeric flavivirus or an attenuated dengue virus comprising the TL-2 Δ30 modification in the 3'UTR of the viral genome. Attenuation of the dengue virus is achieved through the TL-2 Δ30 modification. However, additional attenuating mutations may also be included in one or more components of the vaccine, including, but not limited to: mutations at positions 1495, 1545, 7132, 7163, 7164 and 8308. Attenuating mutations can be achieved by different techniques, including methods known in the art such as through serial passage on tissue culture or through more defined genetic manipulations. Mutations useful for attenuating dengue viruses and chimeric dengue viruses are known in the art. See, e.g. WO 02/095075, WO 2006/44857, U.S. Pat. Nos. 7,189,403, 8,337,860, WO 2003/103571, WO 2000/014245, and WO 2008/022196. Known attenuated dengue strains can also be used in the compositions herein, such as the strains described in WO 06/134433, WO 2006/134443, WO 2007/141259, WO 96/40933, WO 2000/057907, WO 2000/057908, WO 2000/057909, WO 2000/057910, and WO 2007/015783.

Preferred embodiments of the compositions of the invention comprise a tetravalent live attenuated dengue vaccine (LATV). Such tetravalent live attenuated vaccine can comprise four attenuated dengue viruses (LAVs), three LAVs and one attenuated chimeric flavivirus strain (LACV), two dengue LAVs and two LACVs, one dengue LAV and three LACVs, or four LACVs.

In preferred embodiments, the LATV comprises the following features: (1) rDEN1Δ30, which is a DENV1 LAV wherein the DENV1 viral genome comprises a 30 nt deletion corresponding to the TL2 stem-loop structure in the 3' UTR; (2) rDEN2/4Δ30, which is a DENV2 LACV comprising the DENV2 prM and E genes on a DENV4 backbone, wherein the DEN4 backbone comprises a 30-nt deletion corresponding to the TL2 stem-loop structure in the 3' UTR; (3) rDEN3 Δ30/Δ31, which is a DENV3 LAV wherein the DENV3 viral genome comprises a 30 nt deletion corresponding to the TL2 stem-loop structure in the 3' UTR and a separate, noncontiguous, upstream 31 nt deletion corresponding to the TL-3 structure of the 3' UTR; and (4) rDEN4Δ30, which is a DENV4 LAV wherein the DENV4 viral genome comprises a 30 nt deletion corresponding to the TL2 stem-loop structure in the 3' UTR.

In embodiments of the invention comprising chimeric flaviviruses, each chimeric flavivirus comprises a viral genome that comprises nucleotide sequences encoding the prM and E proteins of a single dengue virus serotype and nucleotide sequences that encode the capsid and non-structural proteins (i.e. "the backbone") of a different flavivirus, wherein each of the chimeric flaviviruses are attenuated. Methods for construction of a recombinant live attenuated flavivirus strain may comprise the use of a known attenuated strain as a base, wherein the method comprises substituting the appropriate genes (prM and E) from a related virus of interest for the equivalent genes of the base virus. For example, this approach has been used for WNV wherein the chimeric virus is an intertypic chimeric based on an attenuated DEN-4 strain comprising prM and E genes of WNV (Bray, M. et al., *J. Virol.* (1996) 70:4162-4166; Chen, W., et al., *J. Virol.* (1995) 69:5186-5190; Bray, M. and Lai, C.-J., *Proc. Natl. Acad. Sci. USA* (1991) 88:10342-10346; Lai, C. J. et al., *Clin. Diagn. Virol.* (1998) 10:173-179).

Another approach has been the use of the YF 17D attenuated yellow fever strain as a base to develop recombinant chimeric vaccines, which was previously used for JE virus, DEN viruses, and WN virus. A chimeric yellow fever vaccine can be constructed comprising a yellow fever backbone by replacing the genes coding for prM and E proteins from any yellow fever strain, for example, YFV 17D, with those of a Dengue serotype. After DNA cloning, RNA is transcribed and transfected into Vero cells to obtain chimeric viruses possessing the YFV 17D replication machinery and the external coat of the relevant Dengue virus. See Guirakhoo et al., *Journal of Virology,* 74(12): 5477-5485 (2000); Guy et al., *Vaccine* 28: 632-649 (2010); Monath T. P. *Adv Virus Res* (2003) 61:469-509; Monath et al. *Proc. Natl. Acad. Sci. USA* (2006) 103:6694; and WO 98/37911. Thus, in some embodiments of the invention, the live attenuated dengue vaccine comprises (1) at least one chimeric flavivirus comprising the prM and E proteins of a single dengue serotype and a yellow fever backbone and (2) at least one LAV or LACV which comprises a viral genome comprising a 30-nucleotide deletion of the TL-2 stem-loop structure of the 3'UTR.

Chimeric live attenuated flaviviruses useful in the compositions of the invention may also comprise a dengue chimeric virus, wherein the viral genome comprises prM and E genes of a single dengue virus serotype and the capsid and nonstructural genes of a different dengue virus serotype. In embodiments wherein the chimeric virus comprises a backbone from a second dengue serotype, the dengue backbone comprises a deletion of about 30-nucleotides of the 3'UTR that corresponds to the TL-2 stem-loop structure and may optionally comprise additional attenuating mutations. Any attenuated dengue virus or wild-type dengue virus can be used as the backbone of the chimeric virus, by introduction of a 30-nucleotide deletion of the TL-2 stem-loop structure to an attenuated dengue backbone or wild-type dengue viral backbone. Attenuation of a dengue virus backbone can be achieved through serial passage, through the introduction of defined genetic mutations, or through the use of known attenuated dengue strains. Dengue chimeric vaccines are described, for example, in Whitehead et al. WO 03/092592. In some embodiments of the invention, the live attenuated vaccine comprises a chimeric flavivirus wherein the capsid and nonstructural proteins are from a different dengue serotype than the prM and E proteins.

The dengue virus vaccine compositions of the invention comprise an effective amount of live attenuated virus vaccine. In some embodiments of the invention, the potency of the live attenuated dengue vaccine is from 10 to about $1\times10^7$ plaque forming units (PFU's). In alternative embodiments, the potency of the live attenuated dengue vaccine is from about $1\times10^2$ to about $1\times10^6$ PFU's. In other embodiments, the potency of the live attenuated dengue vaccine is from about $1\times10^3$ to about $1\times10^5$ PFU's.

Dengue Subunit Vaccine

In some embodiments of the invention, the composition comprises a recombinant dengue subunit vaccine which comprises one or more dengue antigen proteins. In preferred embodiments of this aspect of the invention, the recombinant dengue subunit vaccine comprises one or more dengue proteins, fusion proteins, or a fragment or fragments thereof. In further preferred embodiments, the recombinant dengue subunit vaccine comprises dengue envelope or E protein, or a fragment thereof.

In further preferred embodiments, the recombinant dengue subunit vaccine is tetravalent, i.e. targets an immune response against all four dengue serotypes. A recombinant dengue subunit vaccine can comprise four recombinant dengue proteins or less than four, e.g. a recombinant DEN1 protein, a recombinant DEN2 protein, and a recombinant DEN3/4 fusion protein. In some embodiments, the recombinant dengue subunit vaccine comprises dengue virus envelope glycoprotein, or fragments thereof, of DEN1-4 (e.g. DEN1-80E, DEN2-80E, DEN3-80E, DEN4-80E, or DEN4-80EZip) that is produced and secreted using a recombinant expression system. Said subunit vaccine may optionally comprise an adjuvant, as described more fully below.

In some embodiments of this aspect of the invention, the recombinant dengue subunit vaccine comprises one or more purified dengue virus envelope ("E") proteins, a pharmaceutically acceptable excipient, wherein the E proteins each constitute approximately 80% of the length of wild type E starting from amino acid residue 1 at its N-terminus, such that said E protein is secretable into growth medium when expressed recombinantly in a host cell and wherein the composition induces the production of neutralizing antibodies in human subjects. In some embodiments of the invention, the recombinant dengue subunit vaccine further comprises an effective amount of an adjuvant. In some embodiments of the invention, the DEN-4 E protein is dimeric ("DEN4-80EZip"), as described in U.S. Pat. No. 6,749,857 and WO 2012/154202.

In some embodiments of this aspect of the invention, the E proteins in the composition described above are recombinantly produced and expressed in insect host cells. In further preferred embodiments, the E protein is recombinantly produced and expressed in *Drosophila melanogaster* Schneider 2 (S2) host cells.

The recombinant dengue virus E proteins of the present invention can be produced by means of a cell culture expression system that uses *Drosophila* Schneider 2 (S2) cells. This system has been demonstrated to produce recombinant dengue envelope proteins that maintain native-like structure (Cuzzubbo et al., *Clin. Diagn. Lab. Immunol.* (2001) 8:1150-55; Modis et al., *Proc. Natl. Acad. Sci.* (2003) 100:6986-91; Modis et al., *Nature* (2004) 427:313-9; Zhang et al., Structure (2004)12(9):1607-18). This expression system has also been shown to express other recombinant envelope proteins from other flaviviruses such as West Nile, Japanese Encephalitis, hepatitis C, and Tick Borne Encephalitis viruses. The recombinant dengue envelope proteins may be truncated at the C-terminus, leaving 80% of the native envelope protein ("80E"). Thus 80E is defined as approximately the first 80% of consecutive amino acids of E protein starting at amino acid 1 of its N-terminus.

As stated above, some embodiments of this aspect of the invention comprise truncated 80E proteins which consist of approximately 80% of the length of wild type E starting from amino acid residue 1 at its N-terminus. The E proteins used in some embodiments of the invention delete the membrane anchor portion (approximately the last 10% of E at the carboxy end) of the protein. In other words, truncated 80E proteins of use in specific embodiments of the invention consist of up to the first 90% of consecutive amino acids of E starting at amino acid 1 of its N-terminus, thus allowing it to be secreted into the extracellular medium, facilitating recovery. The truncation may further delete the "stem" portion of the E protein that links the 80E portion with the membrane anchor portion; the stem portion does not contain notable antigenic epitopes and therefore is not included in the preferred antigens, DEN1-80E, DEN2-80E, DEN3-80E, DEN4-80E, or DEN4-80EZip. More than 90%, but less than 100%, of the E protein can be cloned and secreted, i.e., the protein can be 90%+ in length, carboxy truncated, and can include a portion of the membrane spanning domain so long as the truncated E protein is secretable. "Secretable" means able to be secreted, and typically secreted, from the transformed cells in the expression system. Thus, one of skill in the art will realize that dengue E proteins that are useful in the compositions and methods of the present invention may vary from the 80% exemplified herein, as long as the protein is secretable. In preferred embodiments of each aspect of the present invention, the DEN E proteins are about 80% in length starting from the N-terminal amino acid of the envelope protein and ending at an amino acid in the range of the $393^{rd}$ to $401^{st}$ amino acid, for example, from amino acid 1 to amino acid 395 of dengue virus type 2. In alternative embodiments of each aspect of the invention, the dengue E protein may be about 75%, about 85%, about 90%, about 95%, or about 98% of the consecutive amino acids of E starting at amino acid 1 of its N-terminus. In exemplary embodiments of aspects of the invention herein, the DEN E protein is approximately 80% of consecutive amino acids of E protein starting at amino acid 1 of its N-terminus; such as DEN1-80E, as set forth in SEQ ID NO:1, DEN2-80E, as set forth in SEQ ID NO:2, DEN3-80E, as set forth in SEQ ID NO:3 and DEN4-80E, as set forth in SEQ ID NO:4.

The secreted E protein may further contain domains which facilitate dimerization, such as in the DEN4-80EZip protein, such that the immunogenicity of the recombinant protein is further enhanced. An exemplary DEN4-80EZip protein comprises an amino acid sequence as set forth in SEQ ID NO:5. In some embodiments of this aspect of the invention, the DEN1, DEN2, and DEN3 80E antigens included in the composition are monomeric and the DEN4 80E antigen is dimeric.

In alternative embodiments of this aspect of the invention, the DEN1-80E, DEN2-80E, DEN3-80E and DEN4-80E proteins in the composition are monomeric. In such embodiments, the DEN4 component is present in an amount that is about 1.5 to about 3 times the individual amounts of DEN1, DEN2, and DEN3 proteins, preferably about 2 times the amount of the DEN1, DEN2, and DEN3 components (proteins). In preferred embodiments of this aspect of the invention, the ratio of DEN1:DEN2:DEN3:DEN4 antigens in the compositions is approximately 1:1:1:2.

In embodiments of the invention comprising dengue E proteins, the amount of each E protein in the composition is from about 0.5 μg to about 500 μg. In alternative embodiments, the amount of each E protein is from about 0.5 μg to about 450 μg, 0.5 μg to about 400 μg, 0.5 μg to about 350 μg, 0.5 μg to about 300 μg, 0.5 μg to about 250 μg, 0.5 μg to about 200 μg, 0.5 μg to about 150 μg, 0.5 μg to about 100 μg, 0.5 μg to about 50 μg, 5.0 μg to about 500 μg, 5.0 μg to about 450 μg, 5.0 μg to about 400 μg, 5.0 μg to about 350 μg, 5.0 μg to about 300 μg, 5.0 μg to about 250 μg, 5.0 μg to about 200 μg, 5.0 μg to about 150 μg, 5.0 μg to about 100 μg, 5.0 μg to about 50 μg, 10 μg to about 500 μg, 10 μg to about 450 μg, 10 μg to about 400 μg, 10 μg to about 350 μg, 10 μg to about 300 μg, 10 μg to about 250 μg, 10 μg to about 200 μg, 10 μg to about 150 μg, 10 μg to about 100 μg, 10 μg to about 50 μg, 25 μg to about 500 μg, 25 μg to about 450 μg, 25 μg to about 400 μg, 25 μg to about 350 μg, 25 μg to about 300 μg, 25 μg to about 250 μg, 25 μg to about 200 μg, 25 μg to about 150 μg, 25 μg to about 100 μg, or 25 μg to about 50 μg. In further preferred embodiments, the amount of each E protein in the composition is from about 1.0 μg to about 100 μg. In still further embodiments, the amount of each E protein in the composition is selected from approximately 10, 20, 30, 40, 50, 60, 70, 80, 90, 100, 150, 200, 250, 300, 350, 400, 450, or 500 μg.

Inactivated Dengue Vaccine

As an alternative to a dengue subunit vaccine in the dengue vaccine co-formulations of the invention, a whole inactivated dengue vaccine or inactivated dengue chimeric vaccine, may also be used. Inactivated dengue vaccines of the co-formulations herein comprise one or more whole inactivated dengue viruses and/or one or more inactivated dengue chimeric viruses. In some embodiments of this aspect of the invention, the inactivated dengue vaccine is tetravalent and comprises whole inactivated DEN1, DEN2, DEN3 and DEN4. In alternative embodiments, the inactivated vaccine comprises four inactivated chimeric dengue viruses. In still other embodiments, the inactivated vaccine is tetravalent and comprises one or more whole inactivated dengue viruses and one or more inactivated dengue chimeric viruses, e.g. an inactivated whole DEN1 virus, an inactivated whole DEN2 virus, an inactivated DEN3 chimeric virus and an inactivated DEN4 chimeric virus. One of skill in the art realizes that any combination of inactivated whole or chimeric DEN viruses may be used in the tetravalent compositions and methods of the invention, as long as the vaccine composition targets all four dengue serotypes.

Inactivated dengue vaccines useful in the compositions and methods of the invention are described in Putnak et al. *Vaccine* 23: 4442-4452 (2005), U.S. Pat. Nos. 6,190,859, 6,254,873 and Sterner et al. WO 2007/002470. Alternatively, dengue virus strains and chimeric dengue strains/chimeric flavivirus strains can be inactivated for use in the compositions and methods of the invention through methods known in the art, e.g., with chemicals, heat or radiation.

Adjuvants

Co-administration of vaccines with compounds that can enhance the immune response against the antigen of interest, known as adjuvants, has been extensively studied. In addition to increasing the immune response against the antigen of interest, some adjuvants may be used to decrease the amount of antigen necessary to provoke the desired immune response or decrease the number of injections needed in a clinical regimen to induce a durable immune response and provide protection from disease.

To that end, the dengue virus vaccine co-formulations of the invention may employ an adjuvant. The adjuvant of the co-formulations described herein can be any adjuvant that performs the desired function, as described above, and does not inactivate or significantly impact the titer of the LAV or LACV of the composition.

Aluminum-based compounds were determined to possess adjuvant activity over 60 years ago (for review, see Lindblad, E. B. *Immunol. and Cell Biol.* 82: 497-505 (2004); Baylor et al. *Vaccine* 20: S18-S23 (2002)). Aluminum adjuvants are generally regarded as safe when used at appropriate dosages. Many have been approved for administration into humans by regulatory agencies worldwide.

Accordingly, aluminum-based compounds, such as aluminum hydroxide ($Al(OH)_3$), aluminum hydroxyphosphate ($AlPO_4$), amorphous aluminum hydroxyphosphate sulfate (AAHS), or so-called "alum" ($KAl(SO_4).12H_2O$) (see Klein et al., Analysis of aluminum hydroxyphosphate vaccine adjuvants by Al MAS NMR., *J. Pharm. Sci.* 89(3): 311-21 (2000)), may be combined with the compositions provided herein. In exemplary embodiments of the invention provided herein, the aluminum adjuvant is aluminum hydroxyphosphate or AAHS, alternatively referred to as "MAA". In alternative embodiments, the aluminum adjuvant is an aluminum phosphate adjuvant, referred to herein as "MAPA". In other embodiments, the adjuvant is aluminum hydroxide.

One of skill in the art will be able to determine an optimal dosage of aluminum adjuvant that is both safe and effective at increasing the immune response to the targeted dengue viruses. For a discussion of the safety profile of aluminum, as well as amounts of aluminum included in FDA-licensed vaccines, see Baylor et al., *Vaccine* 20: S18-S23 (2002). Generally, an effective and safe dose of aluminum adjuvant varies from 50 μg to 1.25 mg elemental aluminum per dose (100 μg/mL to 2.5 mg/mL concentration).

Thus, specific embodiments of the present invention include compositions comprising a live attenuated dengue virus vaccine and a non-replicating vaccine, as described in any embodiment herein, and further comprising an aluminum adjuvant. In some embodiments, the non-replicating vaccine is selected from a recombinant dengue subunit vaccine or an inactivated dengue vaccine. In embodiments of the invention, the dengue compositions comprise an adjuvant which comprises from about 50 μg to about 1.25 mg of elemental aluminum per dose of vaccine. In other embodiments, the aluminum adjuvant per dose of vaccine composition comprises an amount of elemental aluminum ranging from about 100 μg to about 1.0 mg, from about 100 μg to about 900 μg, from about 100 μg to about 850 μg, from about 100 μg to about 800 μg, from about 100 μg to about 700 μg, from about 100 μg to about 600 μg, from about 100 μg to about 500 μg, from about 100 μg to about 400 μg, from about 100 μg to about 300 μg, from about 100 to about 250 μg, from about 200 μg to about 1.25 mg, from about 200 μg to about 1.0 mg, from about 200 μg to about 900 μg, from about 200 μg to about 850 μg, from about 200 μg to about 800 μg, from about 200 μg to about 700 μg, from about 200 μg to about 600 μg, from about 200 μg to about 500 μg, from about 200 μg to about 400 μg, from about 200 μg to about 300 μg, from about 300 μg to about 1.25 mg, from about 300 μg to about 1.0 mg, from about 300 μg to about 900 μg, from about 300 μg to about 850 μg, from about 300 μg to about 800 μg, from about 300 μg to about 700 μg, from about 300 μg to about 600 μg, from about 300 μg to about 500 μg, from about 300 μg to about 400 μg, from about 400 μg to about 1.25 mg, from about 400 μg to about 1.0 mg, from about 400 μg to about 900 μg, from about 400 μg to about 850 μg, from about 400 μg to about 800 μg, from about 400 μg to about 700 μg, from about 400 μg to about 600 μg, from about 400 μg to about 500 μg, from about 500 μg to about 1.25 mg, from about 500 μg to about 1.0 mg, from about 500 μg to about 900 μg, from about 500 μg to about 850 μg, from about 500 μg to about 800 μg, from about 500 μg to about 700 μg, from about 500 μg to about 600 μg, from about 600 μg to about 1.25 mg, from about 600 μg to about 1.0 mg, from about 600 μg to about 900 μg, from about 600 μg to about 850 μg, from about 600 μg to about 800 μg, or from about 600 μg to about 700 μg.

Other adjuvants that may be used in conjunction with the dengue virus vaccine compositions of the invention, include, but are not limited to, adjuvants containing CpG oligonucleotides, or other molecules acting on toll-like receptors such as TLR4 and TLR9 (for reviews, see, Daubenberger, C. A., *Curr. Opin. Mol. Ther.* 9(1):45-52 (2007); Duthie et al., *Immunological Reviews* 239(1): 178-196 (2011); Hedayat et al., *Medicinal Research Reviews* 32(2): 294-325 (2012)), including lipopolysaccharide, monophosphoryl lipid A, and aminoalkyl glucosaminide 4-phosphates. Additional adjuvants useful in the compositions of the invention include immunostimulatory oligonucleotides (IMO's; see, e.g. U.S. Pat. Nos. 7,713,535 and 7,470,674); T-helper epitopes, lipid-A and derivatives or variants thereof, liposomes, calcium phosphate, cytokines, (e.g. granulocyte macrophage-colony stimulating factor (GM-CSF) IL-2, IFN-α, Flt-3L), CD40, CD28, CD70, IL-12, heat-shock protein (HSP) 90, CD134 (OX40), CD137, CoVaccine HT, non-ionic block copolymers, incomplete Freund's adjuvant, chemokines, cholera toxin; *E. coli* heat-labile enterotoxin; pertussis toxin; muramyl dipeptide, muramyl peptide analogues, MF59, SAF, immunostimulatory complexes, biodegradable microspheres, polyphosphazene; synthetic polynucleotides.

Additional adjuvants for use with the compositions described herein are adjuvants containing saponins (e.g. QS21), either alone or combined with cholesterol and phospholipid in the characteristic form of an ISCOM ("immune stimulating complex," for review, see Barr and Mitchell, *Immunology and Cell Biology* 74: 8-25 (1996); and Skene and Sutton, *Methods* 40: 53-59 (2006)). Such adjuvants are referred to herein as "saponin-based adjuvants". In specific embodiments of the compositions and methods provided herein, the mutant toxins and/or toxin proteins are combined with an ISCOM-type adjuvant or "ISCOM", which is an ISCOM matrix particle adjuvant, such as ISCOMATRIX™, which is manufactured without antigen (ISCOM™ and ISCOMATRIX™ are the registered trademarks of CSL Limited, Parkville, Australia).

Methods of Use

Embodiments of the invention also include one or more of the dengue vaccine co-formulations described herein (i) for use in, (ii) for use as a medicament or composition for, or (iii) for use in the preparation of a medicament for: (a) therapy (e.g., of the human body); (b) medicine; (c) inhibition of dengue virus replication, including DEN1, DEN2, DEN3 and/or DEN4; (d) induction of an immune response or a protective immune response against one or more of DEN1, DEN2, DEN3 and/or DEN4; (e) induction of a virus neutralizing antibody response against one or more types of dengue; (f) treatment or prophylaxis of infection by dengue virus; (g) prevention of recurrence of dengue virus infection; (h) reduction of the progression, onset or severity of pathological symptoms associated with dengue virus infection and/or reduction of the likelihood of a dengue virus infection or, (i) treatment, prophylaxis of, or delay in the onset, severity, or progression of dengue-associated disease(s), including, but not limited to: dengue fever, dengue hemorrhagic fever, and dengue shock syndrome. In these uses, the dengue vaccine compositions can optionally be employed in combination with one or more adjuvants (e.g., MAA, aluminum phosphate, aluminum hydroxide such as Alhydrogel®, or other aluminum salt adjuvant, a saponin-based adjuvant such as ISCOMATRIX™ (CSL, Ltd.), a TLR-agonist, or lipid nanoparticles, described herein).

Accordingly, the invention provides methods for the prophylactic and/or therapeutic treatment of dengue virus infection or dengue-associated disease comprising administering one or more of the co-formulations of the invention to a patient in need of treatment.

A "patient" (alternatively referred to herein as a "subject") refers to a mammal capable of being infected with a dengue virus, such as DEN1, DEN2, DEN3, or DEN4. In preferred embodiments, the patient is a human. A patient can be treated prophylactically or therapeutically. Prophylactic treatment provides sufficient protective immunity to reduce the likelihood or severity of a dengue infection or the effects thereof, e.g., dengue fever. Therapeutic treatment can be performed to reduce the severity or prevent recurrence of a dengue infection or the clinical effects thereof.

Prophylactic treatment can be performed using a dengue virus vaccine composition of the invention, as described herein. The composition of the invention can be administered to the general population or to those persons at an increased risk of dengue infection, e.g. those persons who live in or will be travelling to areas of the world in which mosquitoes of the genus *Aedes* are prevalent.

Those "in need of treatment" include those already with a dengue infection (e.g. infected with one or more of DEN1, DEN2, DEN3, or DEN4), as well as those prone to have an infection or any person in which a reduction in the likelihood of infection is desired.

Dengue virus vaccine compositions of the invention can be formulated and administered to a patient using techniques well known in the art. Guidelines for pharmaceutical administration in general are provided in, for example, *Vaccines* Eds. Plotkin and Orenstein, W.B. Sanders Company, 1999; *Remington's Pharmaceutical Sciences* $20^{th}$ *Edition*, Ed. Gennaro, Mack Publishing, 2000; and *Modern Pharmaceutics* $2^{nd}$ *Edition*, Eds. Banker and Rhodes, Marcel Dekker, Inc., 1990.

Accordingly, the invention provides a method for inducing a protective immune response in a patient against a dengue infection comprising the step of administering to the patient an immunologically effective amount of any of the dengue virus vaccine compositions described herein.

Also provided by the invention is a method for treating dengue infection, or for treating any pathological condition associated with dengue infection, such treatment including prophylaxis of infection, and reduction in the severity of clinical symptoms, delay or prevention of the progression of disease, and/or reduction in the likelihood of infection or the clinical symptoms thereof; the method comprising the step of administering to the patient an immunologically effective amount of any of the vaccine compositions as described herein.

Additional embodiments of the invention comprise the administration of two or more compositions of the invention to a patient in a prime/boost regime. Accordingly, the invention relates to a method of preventing or reducing the likelihood of dengue infection in a patient in need thereof, comprising the steps of:

(a) administering a first dengue virus vaccine composition of the invention to the patient;

(b) waiting for a predetermined amount of time to pass after step (a);

(c) administering to the patient a second dengue virus vaccine composition of the invention; and, (d) optionally repeating steps (b) and (c);

whereby the dengue infection is prevented or the likelihood of being infected with dengue is reduced in the patient.

In embodiments of the method above, the dengue virus vaccine compositions of the invention are in the form of a liquid (i.e. the live attenuated dengue vaccine and the non-replicating dengue vaccine are formulated together as a liquid in the same vial or container). In alternative embodiments, the dengue virus vaccine compositions are lyophilized (i.e. the live attenuated dengue vaccine and the non-replicating dengue vaccine are formulated together and lyophilized in the same vial or other container) and reconstituted with a sterile diluent prior to administration to the patient. In additional embodiments, the live attenuated dengue vaccine and the non-replicating dengue vaccine are provided in separate vials or containers and mixed together prior to administration to the patient by the clinician. In such embodiments, the live attenuated dengue vaccine and the non-replicating dengue vaccine can be (1) both in the form of a liquid, (2) both lyophilized, or (3) one vaccine in the form of a liquid and one vaccine lyophilized. When one vaccine is in the form of a liquid and one vaccine is lyophilized, the lyophilized vaccine can be reconstituted with the liquid vaccine to form a dengue virus vaccine composition of the invention or the lyophilized vaccine can be reconstituted with a sterile diluent and then mixed with the liquid vaccine to form a dengue virus vaccine composition of the invention.

The amount of time between the first dose of a dengue virus vaccine composition of the invention and the second dose of a dengue virus vaccine composition of the invention, or any dose thereafter, is from about 2 weeks to about 2 years. In preferred embodiments of the invention, a time of 2 months to 12 months is allowed to pass between multiple administrations. In alternative embodiments of this aspect of the invention, the amount of time between each administration of each dose of vaccine composition is independently selected from the group consisting of 2 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, and 24 months.

In some embodiments of the invention, the first and second dengue virus vaccine compositions are the same. In alternative embodiments, the first and second dengue virus vaccine compositions are not the same.

The dengue virus vaccine compositions of the invention can be administered by different routes. In preferred embodiments of the invention, the compositions of the invention are administered parenterally, i.e. by intradermal, subcutaneous or intramuscular injection. Subcutaneous and intramuscular administration can be performed using, for example, needles or jet-injectors.

The compositions described herein may be administered in a manner compatible with the dosage formulation, and in such amount as is immunologically-effective to treat and/or reduce the likelihood of dengue infection. The dose administered to a patient, in the context of the present invention, should be sufficient to affect a beneficial response in a patient over time such as a reduction in the level of dengue virus, or to reduce the likelihood of infection by dengue. The quantity of the dengue virus vaccines to be administered may depend on the subject to be treated inclusive of the age, sex, weight and general health condition thereof. In this regard, precise amounts of the vaccine required to be administered will depend on the judgment of the practitioner. In determining the effective amount of the vaccine to be administered in the treatment or prophylaxis against dengue infection, the physician may evaluate circulating plasma levels, progression of disease, and the production of anti-dengue antibodies. In any event, suitable dosages of the immunogenic compositions of the invention may be readily determined by those of skill in the art.

Suitable dosing regimens are preferably determined taking into account factors well known in the art including age, weight, sex and medical condition of the patient; the route of administration; the desired effect; and the particular composition employed. The timing of doses depends upon factors well known in the art, and can range from 2 weeks to 24 months. After the initial administration one or more additional doses may be administered to maintain and/or boost antibody titers.

The invention also relates to methods for preventing dengue infection, or preventing or ameliorating the symptoms thereof, comprising the steps of: (a) mixing a live attenuated dengue vaccine and a non-replicating dengue vaccine to form a dengue virus vaccine composition, wherein the first vaccine comprises at least one dengue LAV or LACV, wherein the LAV or LACV comprises a deletion of about 30-nucleotides corresponding to the TL-2 stem-loop structure of the 3'UTR; and (b) administering a dose of the dengue virus vaccine composition of step (a) to a patient in which dengue infection or the symptoms thereof are to be prevented or ameliorated. In this method, the dengue virus vaccine composition is administered to the patient within a time period after mixing in which it remains stable, e.g. within 24 hours. In some embodiments of this aspect of the invention, the non-replicating dengue vaccine is a recombinant dengue subunit vaccine or an inactivated dengue vaccine.

Further embodiments of this aspect of the invention comprise (c) allowing a predetermined amount of time to pass after administration of the dengue virus vaccine composition, and (d) administering a second dose of a composition of the invention. In said embodiments, steps (c) and (d) may optionally be repeated one or more times.

In the method described above the first dengue vaccine is preferably tetravalent and comprises a DEN1, DEN2, DEN3, and DEN 4 component, wherein each component comprises either a live attenuated dengue virus or a live attenuated chimeric flavivirus, as described herein. In exemplary embodiments, the live attenuated dengue vaccine comprises four chimeric flaviviruses; wherein each of the chimeric flavivirus comprises the prM and E proteins of a single dengue virus serotype and the capsid and non-structural proteins of a different flavivirus, wherein the each of the chimeric flavivirus is attenuated. In certain embodiments, the capsid and nonstructural proteins of the four chimeric flaviviruses are from yellow fever virus. In alternative embodiments, the capsid and nonstructural proteins of each of the four chimeric flaviviruses are from a different dengue serotype than the prM and E proteins.

In some embodiments of this aspect of the invention, the second dengue vaccine is a tetravalent recombinant dengue subunit vaccine comprising dengue E proteins, or fragments thereof, from DEN1, DEN2, DEN3, and DEN4. Subunit vaccines useful in this method of the invention are described herein. In preferred embodiments, the E proteins each constitute about 80% of the length of wild type E of DEN1, DEN2, DEN3 and DEN4, starting from amino acid residue 1 at its N-terminus.

In certain embodiments of the method described above, the live, attenuated dengue vaccine is lyophilized and the recombinant subunit vaccine is a liquid prior to mixing. In some embodiments, the mixing of step (a) comprises reconstituting the lyophilized vaccine with the liquid vaccine. In alternative embodiments, the lyophilized vaccine is reconstituted with a sterile diluent prior to mixing with the liquid vaccine in step (a).

All publications mentioned herein are incorporated by reference for the purpose of describing and disclosing methodologies and materials that might be used in connection with the present invention.

Having described different embodiments of the invention herein with reference to the accompanying drawings, it is to be understood that the invention is not limited to those precise embodiments, and that various changes and modifications may be effected therein by one skilled in the art without departing from the scope or spirit of the invention as defined in the appended claims.

EXAMPLE 1

Preparation of Formulations for Compatibility/Stability Testing of Live Attenuated Dengue Viruses in the Presence of Adjuvants and/or Dengue Antigens (Tetravalent DEN-80E).

A study was performed to evaluate the compatibility/stability of recombinant Δ30 live attenuated viruses (rDEN1-4) when co-formulated in combination with a tetravalent DEN-80E (1-4) subunit vaccine (V180), alone or combined with MAA or ISCOMATRIX® (IMX).

All formulations were prepared in a bio-safety cabinet using aseptic technique. Samples for testing were formulated with the desired adjuvant, dengue antigen(s), or adjuvant/antigen(s) combination in Dulbecco's PBS and placed in 2 ml sterile ISO vials sealed with FLUROTEC® (West Pharmaceutical Services, Inc., Exton, Pa.) stoppers. Adjuvants/antigens samples tested in this study were as follows: (1) PBS alone; (2) tetravalent DEN-80E (DEN1-80E+DEN2-80E+DEN3-80E+DEN4-80E); (3) tetravalent DEN-80E+MAA; (4) tetravalent DEN-80E+3×MAA and (5) tetravalent DEN-80E+ISCOMATRIX™ adjuvant (IMX). Adjuvants/antigen samples were field-mixed with the live attenuated dengue viruses in a 1:1 ratio as described below. The dose and concentrations of the samples, prior to and after field mixing with the Δ30 live attenuated dengue viruses (as described in Example 2) were as shown in Table 1.

TABLE 1

Concentration of Tetravalent Test Samples

| S. # | Adjuvant/Antigen | Dose (0.5 ml) | Pre Field Mix Concentration | Post Field Mix Concentration |
|---|---|---|---|---|
| 1 | D-PBS | N/A | N/A | N/A |
| 2 | tetravalent DEN-80E | DEN1-80E- 10 μg<br>DEN2-80E- 10 μg<br>DEN3-80E- 10 μg<br>DEN4-80E- 20 μg | 200 μg/ml DEN-80E (1-4) | 100 μg/ml DEN-80E (1-4) |
| 3 | tetravalent DEN-80E + MAA | DEN1-80E- 10 μg<br>DEN2-80E- 10 μg<br>DEN3-80E- 10 μg<br>DEN4-80E- 20 μg<br>MAA- 225 μg | 200 μg/ml DEN-80E (1-4)<br>900 μg/ml MAA | 100 μg/ml DEN-80E (1-4)<br>450 μg/ml MAA |
| 4 | tetravalent DEN-80E + 3x MAA | DEN1-80E- 10 μg<br>DEN2-80E- 10 μg<br>DEN3-80E- 10 μg<br>DEN4-80E- 20 μg<br>3x MAA- 675 μg | 200 μg/ml DEN-80E (1-4)<br>2700 μg/ml MAA | 100 μg/ml DEN-80E (1-4)<br>1350 μg/ml MAA |
| 5 | tetravalent DEN-80E + IMX | DEN1-80E- 10 μg<br>DEN2-80E- 10 μg<br>DEN3-80E- 10 μg<br>DEN4-80E- 20 μg<br>IMX- 60 ISCO units | 200 μg/ml DEN-80E (1-4)<br>240 ISCO units IMX | 100 μg/ml DEN-80E (1-4)<br>120 ISCO units IMX |

All formulations were stored at 2-8° C. prior to field mixing with LAV.

EXAMPLE 2

Compatibility/Stability Testing of Co-formulations with Δ30 Dengue Live Attenuated Viruses in the Presence of Adjuvants and/or Dengue Antigens (Tetravalent DEN-80E)

Antigen/adjuvant samples prepared in Example 1 were field mixed with MO dengue live attenuated viruses and tested for virus viability using an in vitro plaque assay on Vero cells as described below. The live attenuated dengue viruses used in these studies were (rDEN1-rDEN1Δ30-1545; rDEN2-rDEN2/4 Δ 30(ME)-1495,7163; rDEN3- rDEN3Δ30/31-7164; and rDEN4-rDEN4 Δ 30-7132,7163, 8308). Concentrations of the dengue antigens and adjuvants following field-mixing with the Δ30 LAV are provided in Table 1.

Twenty-four well plates were seeded with $4\times10^5$ Vero cells/well. The passage level of the Vero cells was P144. To dilute viral samples for the plaque assay (T=0 hour time point), a 1 mL aliquot of each of the Δ30 LAV's (rDEN1-4) was thawed in a 22° C. water bath. Dilutions of virus were performed in 2% medium 199 to produce a diluted stock with viral titer of $2\times10^5$ PFU/mL. From this diluted stock, 0.5 mL of virus was aliquoted into a fresh tube and mixed with 0.5 mL of one of the adjuvant/antigen formulations described in Example 1 to give a 1:1 dilution. The total volume obtained was 1 mL, of which 0.5 mL was used for the T=0 hours plaque assay and 0.5 mL was stored at 4° C. for use in T=24 time point plaque assay.

Further dilutions of the 1:1 Δ30LAV:adjuvant/antigen samples were prepared in a 96-well plate using 2% medium 199 to give 1:10, 1:100, 1:1,000, 1:10,000, 1:100,000 and 1:1,000,000 dilutions of each test sample. To perform the assay, Vero cells monolayers were washed with PBS and 75 μl of each diluted sample (in duplicate) was added to each well of the plates. Virus inoculum was spread onto the cells in the well and the plates were placed in an incubator. The plates were rocked every 10-15 min for 1 hour to evenly spread the inoculum. After 1 hour of adsorption, cells were overlaid by adding 1 ml of 1% methyl cellulose in culture medium to each well and incubated at 37° C. with 5% $CO_2$.

After 6 days of incubation, the methyl cellulose overlay from each well was aspirated off and the cell monolayer was subjected to immunostaining using a pan-flavivirus monoclonal antibody 4G2 (Henchal et al. Dengue virus-specific and flavivirus group determinants identified with monoclonal antibodies by indirect immunofluorescence. *The American Journal of Tropical Medicine and Hygiene* 31 (4):830-836 (1982)). Following the immunostaining procedure, virus titer was determined by counting the number of plaques at appropriate virus dilution.

Figure 2:
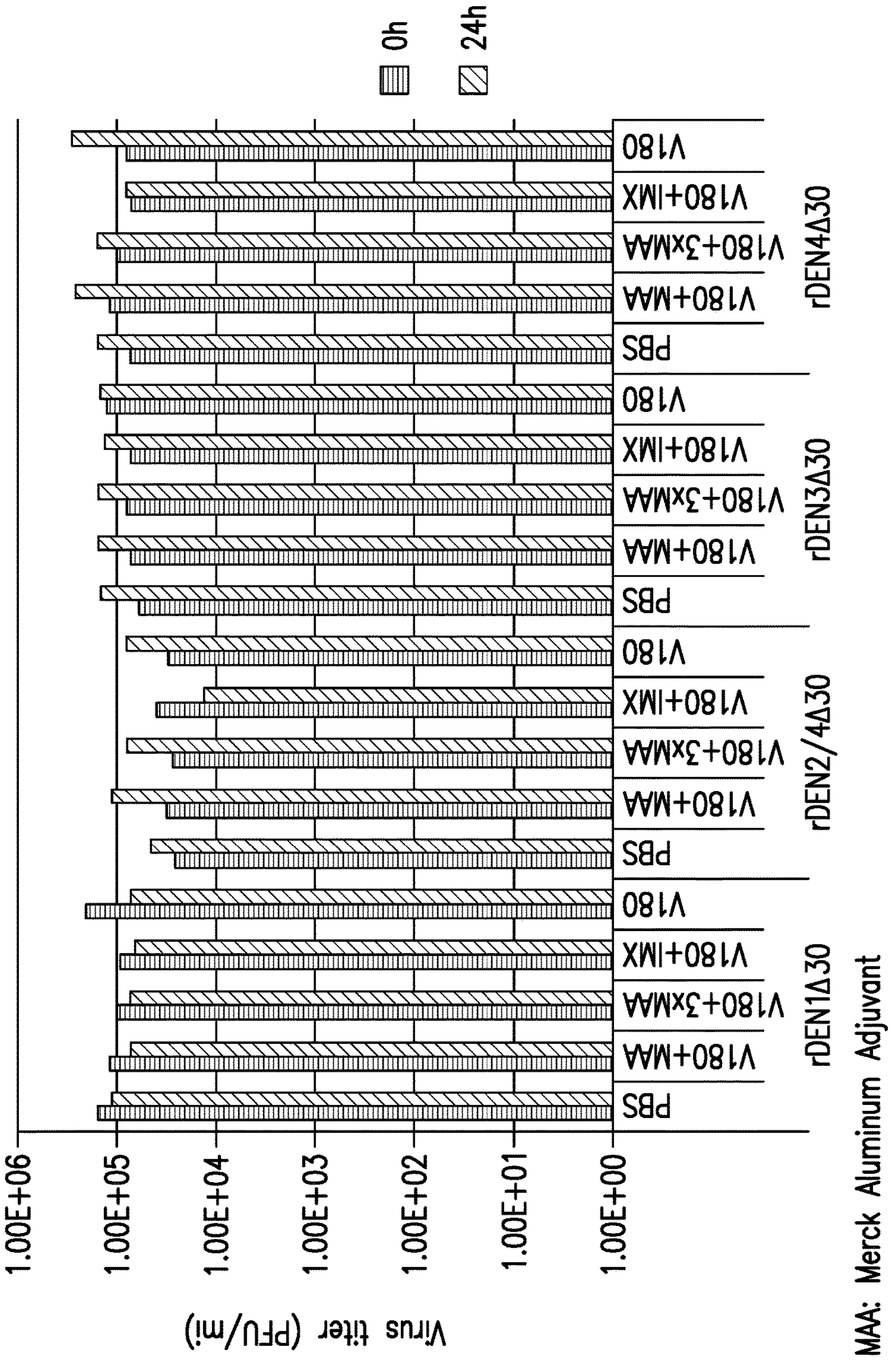
FIG. 2 shows the effect of mixing the indicated adjuvants and subunit dengue antigens on virus viability for dengue virus type 1 (“rDEN1Δ30” bars on chart), dengue virus type 2 (“rDEN2/4Δ30” bars), dengue virus type 3 (“rDEN3Δ30” bars), and dengue virus type 4 (“rDEN4Δ30” bars) in the Δ30 LATV described above and in Example 1. Virus viability (reported as viral titer in PFU/ml) was determined using an in vitro plaque assay on Vero cells as described in Example 2. Shown are values for the initial time-point (0 hours) for each sample compared to the same mixtures after 24 hours of storage at 4° C.

After 24 hours, the procedure above was repeated to determine the viral titer of each sample after storage. Samples were prepared as described above. Results indicate that none of the tested adjuvants, subunit antigen alone or adjuvant/antigen formulations had any effect on viral titer of the Δ30 LAV's at T=0 (see FIG. 2). The results further indicate that the Δ30 LAV's were stable with subunit antigens alone and with adjuvants even after 24 hours of incubation at 4° C.

EXAMPLE 3

Evaluation of Dengue Prime-Boost Vaccination Strategies in *Macaca mulatta*

The objective of this non-GLP study conducted in Rhesus macaques was to evaluate the co-formulation prime-boost vaccination strategy and compare it to a conventional prime boost strategy. For the study, two vaccine candidates, a tetravalent recombinant dengue subunit vaccine candidate (V180) and a Δ30 tetravalent dengue live attenuated vaccine (Δ30 LAV) were administered using different regimens. The tetravalent V180 candidate comprised truncated envelope glycoproteins (DEN-80E) from each of the 4 dengue virus serotypes (Dengue Virus (DENV) 1, DENV2, DENV3, and DENV4). The Δ30 tetravalent LAV comprised live attenuated dengue viruses of dengue types 1-4 (rDEN1–rDEN1Δ30-1545; rDEN2–rDEN2/4 Δ30(ME)-1495,7163; rDEN3–rDEN3Δ30/31-7164; and rDEN4–rDEN4 Δ 30-7132,7163,8308).

Healthy adult, Indian rhesus macaques of either sex (n=4/group), weighing more than 3 kg, and which were flavivirus (DENV 1, 2, 3 and 4, and West Nile Virus) antibody-negative by ELISA, were utilized in this study. Vaccines were administered as described in Table 2. For the study, Group 1 received the Δ30 LAV vaccine subcutaneously (SC) at 0 and 16 weeks. Group 2 received a conventional prime boost in which the Δ30 LAV vaccine was given at 0 weeks followed by V180 formulated with Alhydrogel® (Brenntag Biosector, Frederikssund, DK) at 16 weeks. Group 3 received co-formulations of the Δ30 LAV vaccine and V180/Alhydrogel® at 0 and 16 weeks (co-formulation prime boost). All vaccines were administered at 0.5 mL per dose. After vaccination, the animals were observed daily for any changes at the inoculation site or other changes in activity or feeding habits that might indicate an adverse reaction to the vaccine.

TABLE 2

Schedule and Formulations Used in Rhesus Macaque Immunogenicity Study

| Group | Animal ID | Formulation/Schedule Week 0 | Week 16 |
|---|---|---|---|
| 1 | A10R070<br>A7E030<br>A7X034<br>03D350 | Δ30 LAV (10e5 pfu each LAV)<br>Administered SC (0.5 ml) | Δ30 LAV (10e5 pfu each)<br>Administered SC (0.5 ml) |
| 2 | A10L106<br>A7E017<br>05D039<br>04D300 | Δ30 LAV (10e5 pfu each LAV)<br>Administered SC (0.5 ml) | Tetravalent DEN-80E<br>(10, 10, 10, 20 μg each 80E)/<br>Alhydrogel ® (225 μg)<br>Administered IM (0.5 ml) |
| 3 | A10R080<br>A7E078<br>99D174<br>03D329 | Δ30 LAV (10e5 pfu each LAV)/<br>Tetravalent DEN-80E<br>(10, 10, 10, 20 μg each 80E)/<br>Alhydrogel ® (225 μg)<br>Administered IM (0.5 ml) | Δ30 LAV (10e5 pfu each LAV)/<br>Tetravalent DEN-80E<br>(10, 10, 10, 20 μg each 80E)/<br>Alhydrogel ® (225 μg)<br>Administered IM (0.5 ml) |

Virus-neutralizing activity was determined every 4 weeks through study week 20 using the LiCor-based microneutralization assay. For the LiCor assay, Vero cells were seeded overnight in 100 μl 10% media 199 in flat-bottom 96-well tissue culture plates at $1.5\times10^4$ cells/well. In separate 96-well plates, serum samples were serially diluted 2-fold in duplicate for 8 dilutions beginning at 1:10. For samples that failed to reach an end-point titration, the sample was retested beginning at a higher dilution. Serum was incubated with an equal volume of virus diluted to 50 pfu/well. All assay dilutions were performed in 2% media 199. The mixture was incubated at 37° C.+5% $CO_2$ for 1 hour. Following neutralization, the entire mixture was added onto the plated Vero cells and incubated for 4 days at 37° C.+5% $CO_2$. Following removal of culture media, cells were fixed with 3.7% formaldehyde in PBS for 30 minutes. Plates were washed 2 times for 5 minutes each with 200 μl 0.1% Titon X-100/PBS. Plates were stained with 50 ul of 4G2 antibody at 2.8 μg/ml. A biotinylated horse anti-mouse IgG was then added at 7.5 μg/ml followed by a cocktail of IRDye® 800CW Streptavidin (1:1000) and DRAQS fluorescent probe (1:10,000). Plates were kept in the dark for this final development. Antibodies and reagents were diluted in Odyssey Block buffer supplemented with 0.2% Tween-20. Plates were washed 3 times between antibody exchanges using 0.1% Tween-20/PBS. Incubation steps were performed for 1 hour at room temperature. Washing and dispensing steps were automated using the BioTek® EL406 plate washer system (Winooski, Vt.). Plates were air-dried and scanned with an infrared Odyssey® Sa imaging system (Li-Cor Biosciences). Raw data was imported into an Excel processing worksheet. Duplicate wells were averaged and serum end-point neutralization titers were defined as the reciprocal of the highest serum dilution that reduces the 800 nm/700 nm fluorescence integrated intensity ratio ≥50% when compared to virus control included on each assay plate. Prism® (GraphPad Software, Inc.) was used to plot results. All samples were setup beginning at a 1:10 dilution. If a sample failed to neutralize at this dilution a titer of 1:5 was assigned.

The geometric mean neutralization titers for DENV1, DENV2, DENV3 and DENV4 for all groups for Week 4 (4 weeks post dose 1) are summarized in FIG. 3. At this time point, virus-neutralizing antibody responses were detected in all immunized animals except for one animal that did not respond to DENY 4 in group 2. Key conclusions from the Week 4 results are:

- The neutralization responses measured in the co-formulation group (Groups 3) at four weeks post dose 1 were comparable to those induced when the Δ30 LATV vaccine was given alone (Groups 1 and 2). This indicates that the co-formulation of the Δ30 LATV vaccine with the V180 subunit vaccine and Alhydrogel® adjuvant does not negatively impact the response to the first dose of live attenuated virus vaccine.

The geometric mean neutralization titers for DENV1, DENV2, DENV3 and DENV4 for all groups for Week 20 (4 weeks post dose 2) are summarized in FIG. 4. At this time point, virus-neutralizing antibody responses were detected in all immunized animals. Key conclusions from the Week 20 results are:

- Both the conventional prime boost (Group 2) and the co-formulation prime boost approaches (Group 3) induced superior neutralization titers to all four DENV types compared to the Δ30 LATV vaccine (Group 1). Titers ranged from 1.7 to 6.7 fold higher depending on the DENV type.
- The neutralization responses measured in the co-formulation group (Groups 3) at four weeks post dose 2 were equivalent to if not better than those induced in the groups receiving the conventional prime-boost regimen (Group 2). This indicates that the co-formulation of the Δ30 LATV vaccine with the V180 subunit vaccine and Alhydrogel® adjuvant does not negatively impact the response to the subunit boost.

Figure 5:
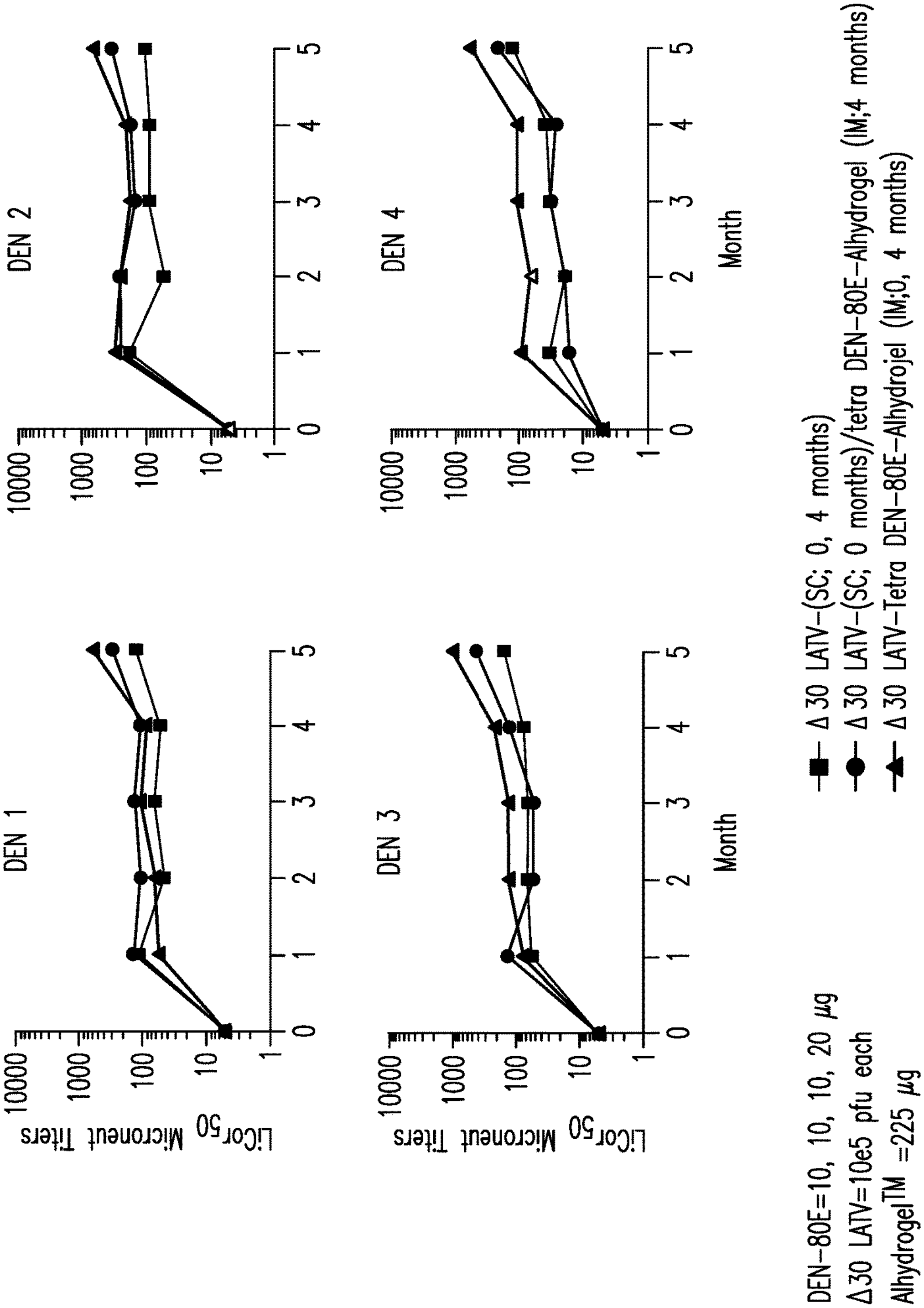
FIG. 5 provides the longitudinal geometric mean neutralization titers for DENV1, DENV2, DENV3 and DENV4 for all groups described in Example 3.

The longitudinal geometric mean neutralization titers for DENV1, DENV2, DENV3 and DENV4 for all groups are shown in FIG. 5. Overall, the data demonstrate that the co-formulation prime boost regimen elicits responses that are comparable to the conventional prime boost approach and that the responses are superior the Δ30 LATV given as a homologous vaccine.

EXAMPLE 4

Evaluation of Dengue Prime-Boost Dose-dependent Vaccination Strategies in *Macaca mulatta*

The objective of this non-GLP study conducted in Rhesus macaques was to evaluate the co-formulation prime-boost vaccination strategy using different coformulation doses of subunit vaccine and dengue live attenuated vaccine. For the study, the two vaccine candidates described in Example 3 were used.

Healthy adult, Indian rhesus macaques of either sex (n=5/group), weighing more than 4 kg, and which were flavivirus (DENV 1, 2, 3 and 4, and West Nile Virus) antibody-negative by ELISA, were utilized in this study. Vaccines were administered as described in Table 3. For the study, Group 1 received the Δ30 LAV vaccine (10e5 pfu each LAV) subcutaneously (SC) at 0 and 24 weeks. Group 2 received co-formulations of the Δ30 LAV vaccine (10e5 pfu each LAV) and V180 (10, 10, 10, 20 μg each 80E)/ Alhydrogel® (Brenntag Biosector, Frederikssund, DK) at 0 and 24 weeks (co-formulation prime boost). Group 3 received co-formulations of the Δ30 LAV vaccine (10e5 pfu each LAV) and V180 (3, 3, 3, 6 μg each 80E)/Alhydrogel® at 0 and 24 weeks (co-formulation prime boost). Group 4 received co-formulations of the Δ30 LAV vaccine (10e3 pfu each LAV) and V180 (10, 10, 10, 20 μg each 80E)/Alhydrogel® at 0 and 24 weeks (co-formulation prime boost). All vaccines were administered at 0.5 mL per dose. After vaccination, the animals were observed daily for any changes at the inoculation site or other changes in activity or feeding habits that might indicate an adverse reaction to the vaccine.

TABLE 3

Schedule and Formulations Used in Rhesus Macaque Immunogenicity Study

| | | Formulation/Schedule | |
|---|---|---|---|
| Group | Animal ID | Week 0 | Week 24 |
| 1 | A11R048<br>A5R027<br>05D087<br>A6L078<br>A6L062 | Δ30 LAV (10e5 pfu each LAV)<br>Administered SC (0.5 ml) | Δ30 LAV (10e5 pfu each)<br>Administered SC (0.5 ml) |

TABLE 3-continued

Schedule and Formulations Used in Rhesus Macaque Immunogenicity Study

| Group | Animal ID | Formulation/Schedule Week 0 | Week 24 |
|---|---|---|---|
| 2 | A10L099 | Δ30 LAV (10e5 pfu each LAV)/ | Δ30 LAV (10e5 pfu each LAV)/ |
| | A5R062 | Tetravalent DEN-80E | Tetravalent DEN-80E |
| | 07D122 | (10, 10, 10, 20 μg each 80E)/ | (10, 10, 10, 20 μg each 80E)/ |
| | A5R007 | Alhydrogel ® (225 μg) | Alhydrogel ® (225 μg) |
| | A6R031 | Administered IM (0.5 ml) | Administered IM (0.5 ml) |
| 3 | A10L121 | Δ30 LAV (10e5 pfu each LAV)/ | Δ30 LAV (10e5 pfu each LAV)/ |
| | 07D066 | Tetravalent DEN-80E | Tetravalent DEN-80E |
| | 05D002 | (3, 3, 3, 6 μg each 80E)/ | (3, 3, 3, 6 μg each 80E)/ |
| | 05D287 | Alhydrogel ® (225 μg) | Alhydrogel ® (225 μg) |
| | 05D230 | Administered IM (0.5 ml) | Administered IM (0.5 ml) |
| 4 | A11L121 | Δ30 LAV (10e3 pfu each LAV)/ | Δ30 LAV (10e3 pfu each LAV)/ |
| | 05D107 | Tetravalent DEN-80E | Tetravalent DEN-80E |
| | A6R011 | (10, 10, 10, 20 μg each 80E)/ | (10, 10, 10, 20 μg each 80E)/ |
| | 05D273 | Alhydrogel ® (225 μg) | Alhydrogel ® (225 μg) |
| | A6L018 | Administered IM (0.5 ml) | Administered IM (0.5 ml) |

Virus-neutralizing activity was determined every 4 weeks through study week 28 using the LiCor-based microneutralization assay as described above in Example 3.

The geometric mean neutralization titers for DENV1, DENV2, DENV3 and DENV4 for all groups for Week 4 (4 weeks post dose 1) are summarized in FIG. 6. At this time point, virus-neutralizing antibody responses were detected in all immunized animals except for one animal in group 1 and one animal in group 4 that did not respond to DENV 1. Key conclusions from the Week 4 results are:

The neutralization responses measured in the co-formulation groups (Groups 2, 3 and 4) at four weeks post dose 1 were comparable to those induced when the Δ30 LATV vaccine was given alone (Group 1). This indicates that the co-formulation of the Δ30 LATV vaccine with the V180 subunit vaccine and Alhydrogel® adjuvant does not negatively impact the response to the first dose of live attenuated virus vaccine.

The neutralization responses in the co-formulation groups that received a high dose (10e5 pfu each virus) of Δ30 LATV (group 2) or low dose (10e3 pfu each virus) of Δ30 LATV (group 4) were comparable. This indicates that a lower dose of the Δ30 LATV vaccine is not negatively impacted by co-formulation with the V180 subunit vaccine and Alhydrogel®.

The geometric mean neutralization titers for DENV1, DENV2, DENV3 and DENV4 for all groups for Week 28 (4 weeks post dose 2) are summarized in FIG. 7. At this time point, virus-neutralizing antibody responses were detected in all immunized animals. Key conclusions from the Week 28 results are:

All co-formulation groups (Groups 2, 3, and 4) demonstrated a strong boost in LiCor Neutralization titers at four weeks post dose 2 that were superior to those seen in the Δ30 LATV only group (group 2). This indicates that the co-formulation of the Δ30 LATV vaccine with the V180 subunit vaccine and Alhydrogel® adjuvant does not negatively impact the response to the subunit boost.

The co-formulation containing the low dose V180 (group 3) boosted as well as the co-formulation containing high dose V180 (group 2).

The co-formulation containing the low dose (10e3 pfu each virus) of Δ30 LATV (group 4) boosted as well as the co-formulation containing high dose high dose (10e5 pfu each virus) of Δ30 LATV (group 2).

Figure 8:
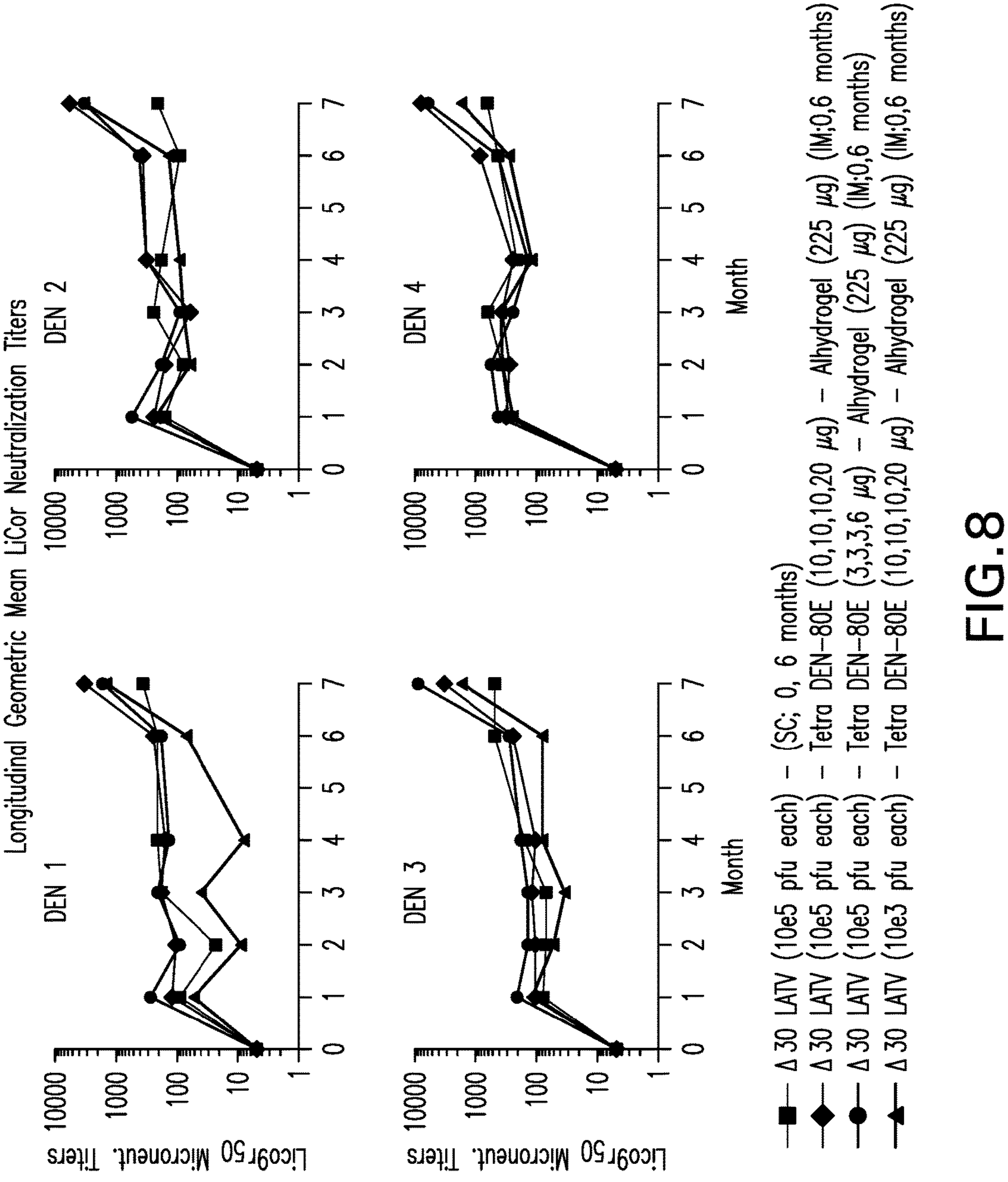
FIG. 8 provides the longitudinal geometric mean neutralization titers for DENV1, DENV2, DENV3 and DENV4 for all groups described in Example 4.

The longitudinal geometric mean neutralization titers for DENV1, DENV2, DENV3 and DENV4 for all groups are shown in FIG. 8. Overall, the data demonstrate that the co-formulation prime boost regimen elicits responses that are comparable to the conventional prime boost approach and that the responses are superior the Δ30 LATV given as a homologous vaccine.

What is claimed is:

1. A dengue virus immunogenic composition comprising a pharmaceutically effective amount of:

(a) a tetravalent live attenuated dengue immunogenic composition comprising at least one live attenuated dengue virus (LAV) or at least one live attenuated chimeric flavivirus (LACV), wherein the LAV and the LACV comprise a viral genome that contains a deletion of about 30 nucleotides corresponding to the TL-2 stem-loop structure of the 3' untranslated region (UTR), wherein the about 30 nucleotides corresponds to nucleotides 172 to 143 from the 3' end of the viral genome; and (b) a tetravalent dengue subunit immunogenic composition which comprises truncated dengue E proteins, or fragments thereof, from dengue virus type 1 (DEN1), dengue virus type 2 (DEN2), dengue virus type 3 (DEN3), and dengue virus type 4 (DEN4), wherein each of the truncated dengue E proteins constitute about 80% of the length of wild type dengue E proteins of DEN1, DEN2, DEN3and DEN4, respectively, starting from amino acid residue 1 at its N-terminus.

2. The composition of claim 1, further comprising an adjuvant.

3. The composition of claim 2, wherein the adjuvant is an aluminum salt adjuvant.

4. The composition of claim 3, wherein the amount of elemental aluminum in the composition is from about 50 μg to about 1.25 mg.

5. The composition of claim 4, wherein the amount of elemental aluminum in the composition is from about 200 μg to about 850 μg.

6. The composition of claim 2, wherein the adjuvant is a saponin-based adjuvant.

7. The composition of claim 1, wherein the amount of each E protein in the composition is from about 0.5 μg to about 500 μg.

8. The composition of claim 7, wherein the amount of each E protein in the composition is from about 1.0 μg to about 100 μg.

9. The composition of claim 8, wherein the amount of DEN4 E protein is about 1.5 to about 2.5 times the amount of each of DEN1, DEN2,and DEN3 E proteins.

10. The composition of claim 7, wherein each E protein is recombinantly produced and expressed in insect host cells.

11. The composition of claim 1, wherein the live attenuated dengue immunogenic composition comprises one LACV that is immunogenic against dengue serotype 2 and three LAVs that are immunogenic against dengue serotypes 1, 3, and 4 wherein the one LACV and the three LAVs each comprise a viral genome that contains a deletion of about 30 nucleotides corresponding to the TL-2 stem-loop structure of the 3' untranslated region (UTR), wherein the about 30 nucleotides corresponds to nucleotides 172 to 143 from the 3' end of the viral genome.

12. The composition of claim 11, wherein the viral genome of the LACV comprises preMembrane (prM) and envelope (E) genes of dengue serotype 2 and capsid and non-structural genes of a different dengue serotype.

13. The composition of claim 12, wherein the different dengue serotype is dengue serotype 4.

14. The composition of claim 1, wherein the live attenuated dengue immunogenic composition comprises a LAV that is immunogenic against dengue serotype 3, wherein the viral genome of the LAV further contains a deletion of nucleotides upstream from the Δ30 deletion corresponding to the TL-3 structure of the 3' UTR.

15. The composition of claim 1, wherein the potency of the live attenuated dengue immunogenic composition is from 10 to about $1\times10^7$ plaque forming units (PFU's).

16. The composition of claim 15, wherein the potency of the live attenuated dengue immunogenic composition is from about $1\times10^3$ to about $1\times10^5$ PFU's.

17. A method of (i) inducing an immune response against dengue, (ii) reducing the likelihood of dengue infection, or (iii) preventing or ameliorating the symptoms of dengue infection, in a patient in need thereof, comprising administering an effective amount of the dengue virus immunogenic composition of claim 1 to the patient.

18. A method of reducing the likelihood of dengue infection, or preventing or ameliorating the symptoms of dengue infection, comprising the steps of:

(a) mixing a first and a second dengue immunogenic composition to form a dengue virus immunogenic composition, wherein the first dengue immunogenic composition is a tetravalent live attenuated dengue immunogenic composition comprising at least one live attenuated dengue virus (LAV) or at least one live attenuated chimeric flavivirus (LACV), wherein the LAV and the LACV comprise a viral genome that contains a deletion of about 30 nucleotides corresponding to the TL-2 stem-loop structure of the 3' untranslated region (UTR), wherein the about 30 nucleotides corresponds to nucleotides 172 to 143 from the 3' end of the viral genome; and wherein the second dengue immunogenic composition is a tetravalent dengue subunit immunogenic composition which comprises truncated dengue E proteins, or fragments thereof, from dengue virus type 1 (DEN1), dengue virus type 2 (DEN2), dengue virus type 3 (DEN3), and dengue virus type 4 (DEN4), wherein each of the truncated dengue E proteins constitute about 80% of the length of wild type dengue E proteins of DEN1, DEN2, DEN3 and DEN4, respectively, starting from amino acid residue 1 at its N-terminus; and (b) administering the dengue virus immunogenic composition of step (a) to a patient in need thereof.

19. A method of reducing the likelihood of dengue infection, in a patient in need thereof, comprising the steps of:

(a) administering a first dengue virus immunogenic composition according to claim 1 to the patient;

(b) waiting for a predetermined amount of time to pass after step (a); and (c) administering to the patient a second dengue virus immunogenic composition according to claim 1; whereby the likelihood of being infected with dengue is reduced in the patient.

* * * * *